(12) United States Patent
Maynard et al.

(10) Patent No.: US 6,656,941 B2
(45) Date of Patent: Dec. 2, 2003

(54) ARYL SUBSTITUTED TETRAHYDROINDAZOLES

(75) Inventors: George Maynard, Clinton, CT (US); Pamela Albaugh, Carmel, IN (US); Stanislaw Rachwal, Branford, CT (US); Linda Gustavson, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/947,702

(22) Filed: Sep. 6, 2001

(65) Prior Publication Data

US 2002/0055524 A1 May 9, 2002

Related U.S. Application Data

(60) Provisional application No. 60/230,256, filed on Sep. 6, 2000.

(51) Int. Cl.[7] .................. A61K 31/50; C07D 403/06
(52) U.S. Cl. ................. 514/252.06; 514/338; 544/238; 546/275.7
(58) Field of Search ............. 544/238; 546/275.7; 548/360.1; 514/252.06, 338

(56) References Cited

FOREIGN PATENT DOCUMENTS

| | | |
|---|---|---|
| GB | 2 352 631 A | 2/2001 |
| WO | WO 97 26243 A | 7/1997 |
| WO | WO 99/25684 A | 5/1999 |
| WO | WO 00/40565 A | 7/2000 |
| WO | WO 00 68691 A | 11/2000 |
| WO | WO 01/16103 A | 3/2001 |

Primary Examiner—Joseph K. McKane
Assistant Examiner—Kamal Saeed
(74) Attorney, Agent, or Firm—McDonnell Boehnen Hulbert & Berghoff

(57) ABSTRACT

Disclosed are compounds of the formula

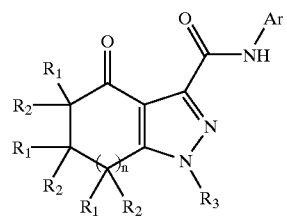

and the pharmaceutically acceptable salts thereof wherein the variables $R_1$, $R_2$, $R_3$, n, and Ar are defined herein. These compounds are highly selective agonists, antagonists or inverse agonists for $GABA_A$ brain receptors or prodrugs of agonists, antagonists or inverse agonists for $GABA_A$ brain receptors and are therefore useful in the diagnosis and treatment of anxiety, depression, Down Syndrome, sleep and seizure disorders, overdose with benzodiazepine drugs and for enhancement of memory.

45 Claims, No Drawings

ARYL SUBSTITUTED TETRAHYDROINDAZOLES

This application claims priority from U.S. Provisional Application Ser. No. 60/230,256, filed Sep. 6, 2000, which is hereby incorporated by reference in its entirety.

BACKGROUND OF THE INVENTION

1. Field of the Invention

This invention provides aryl substituted tetrahydroindazoles, and more specifically to aryl substituted tetrahydroindazoles that bind to the benzodiazepine site of $GABA_A$ receptors. This invention also relates to pharmaceutical compositions comprising such compounds and to the use of such compounds in treatment of central nervous system (CNS) diseases.

2. Description of the Related Art

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg *Science* 1989; 245:1389–1392 and Knight et. al., *Recept. Channels* 1998; 6:1–18). Evidence such as message distribution, genome localization and biochemical study results suggest that the major naturally occurring receptor combinations are $α_1β_2γ_2$, $α_2β_3γ_2$, $α_3β_3γ_2$, and $α_5β_3γ_2$, (Mohler et. al., *Neuroch. Res.* 1995; 20(5): 631–636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, $6^{th}$ ed., 1991, pp. 145–148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of other CNS active compounds. For example, there is evidence that selective serotonin reuptake inhibitors (SSRIs) may show greater antidepressant activity when used in combination with $GABA_A$ selective ligands than when used alone.

International Application WO 00/40565 discloses tetrahydroindazole derivatives.

SUMMARY OF THE INVENTION

This invention provides aryl substituted tetrahydroindazoles, that preferably bind with both high affinity and high selectivity to the benzodiazepine site of the $GABA_A$ receptor, including human $GABA_A$ receptors.

Thus, the invention provides compounds of Formula I, and pharmaceutical compositions comprising compounds of Formula I.

The invention further comprises methods of treating patients suffering from CNS disorders with an effective amount of a compound of the invention. The patient may be a human or other mammal. Treatment of humans, domesticated companion animals (pet) or livestock animals suffering from CNS disorders with an effective amount of a compound of the invention is encompassed by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of $GABA_A$ receptors in tissue sections.

Accordingly, a broad aspect of the invention is directed to compounds of Formula I

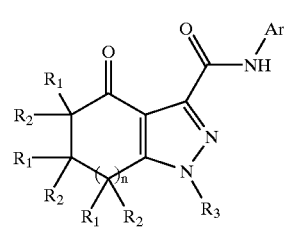

Formula I or a pharmaceutically acceptable salt thereof, wherein:
n is 0, 1, or 2;
$R_1$ and $R_2$ are independently selected from hydrogen, halogen, hydroxy, alkyl, alkenyl, alkynyl, alkoxy, haloalkyl, haloalkoxy, nitro, cyano, amino, and mono- or dialkylamino;
$R_3$ is hydrogen or $C_{1-6}$ alkyl;
Ar is aryl or a saturated, unsaturated, or aromatic heterocyclic group, wherein each aryl of heterocyclic group is optionally substituted;
  when n is 0 or 2, Ar is optionally substituted with G, when n is 1 Ar is substituted by at least one group G, where G represents a group of the formula:

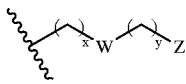

where
W is oxygen, NH, N-alkyl, N-acyl, sulfur, or $CR_5R_6$ where $R_5$ and $R_6$ are the same or different and represent hydrogen, alkyl, or $R_5$ and $R_6$ may be taken together to form a saturated or partially unsaturated carbocyclic ring having 3–7 carbon atoms;

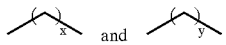

independently represent straight or branched carbon chains which may be substituted with one, two or three substituents independently selected from the group consisting of halogen, hydroxy, cyano, nitro, amino, mono or dialkylamino, alkyl, alkenyl, alkynyl, cycloalkyl, alkoxy, haloalkyl, and haloalkoxy;

x is 0, 1, 2, or 3;
y is 0, 1, 2, or 3;
Z is hydrogen, hydroxy, alkoxy, cycloalkyl, cycloalkyl (alkoxy), amino, mono or dialkylamino, or —$NR_7COR_8$ where $R_7$ and $R_8$ are the same or different and represent hydrogen or alkyl, or $R_7$ and R8 and the atoms to which they are attached form a heterocycloalkyl ring, or
Z is aryl or a saturated, partially unsaturated, or aromatic heterocyclic group of from 1 to 3 rings, 5 to 8 ring members in each ring and, in at least one of said rings, from 1 to about 3 heteroatoms selected from the group consisting of N, O, and S, wherein each aryl or heterocyclic group optionally substituted.

The invention also provides intermediates and methods of making the compounds of the invention.

DETAILED DESCRIPTION OF THE INVENTION

Preferred compounds of Formula I are those where $R_1$ and $R_2$ groups include hydrogen, methyl, and ethyl with hydrogen being particularly preferred, $R_3$ is preferably hydrogen or methyl, Ar is preferably phenyl or pyridyl.

Particular compounds of Formula I include compounds wherein:
$R_1$ and $R_2$ are independently chosen at each occurrence from: hydrogen, halogen, hydroxy, $C_{1-6}$ alkyl, $C_{2-6}$ alkenyl, $C_{2-6}$ alkynyl, $C_{1-6}$ alkoxy, $C_{1-6}$ haloalkyl, $C_{1-6}$ haloalkoxy, nitro, cyano, amino, mono- or di($C_{1-6}$) alkylamino;
Ar is phenyl, pyrrolyl, furanyl, pyrazolyl, imidazolyl, pyridyl, pyrimidinyl, pyrazinyl, pyridizinyl, naphthyl, indolyl, quinolinyl, or isoquinolinyl, each of optionally mono-, di-, or trisubstituted with substituents independently chosen from halogen, cyano, nitro, $C_{1-6}$haloalkoxy, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$) alkyl, halo($C_{2-3}$)alkenyl, halo($C_{2-3}$)alkynyl, $C_{1-6}$ alkoxy, mono or di($C_{1-6}$)alkylamino, and G, with the proviso that when n is 1 Ar is substituted by at least one group G;

G is a group of the formula:

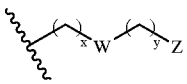

where
W is oxygen, NH, N-acyl, N-alkyl, sulfur, or $CR_5R_6$ where $R_5$ and $R_6$ are the same or different and represent hydrogen, straight or branched chain $C_{1-6}$ alkyl, or $R_5$ and $R_6$ may be taken together to represent a cyclic moiety having 3–7 carbon atoms;
Z is hydrogen, hydroxy, alkoxy, cycloalkyl, cycloalkyl (alkoxy), amino, mono or dialkylamino, or —$NR_7COR_8$ where $R_7$ and $R_8$ are the same or different and represent hydrogen or alkyl, or
Z is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, quinoxalinyl, morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{2-6}$alkenyl, $C_{2-6}$alkynyl, $C_{3-7}$cycloalkyl, $C_{3-7}$ cycloalkyl($C_{1-3}$)alkyl, $C_{1-3}$haloalkoxy, halo($C_{1-3}$) alkyl, halo($C_{2-3}$)alkenyl, halo($C_{2-3}$)alkynyl, $C_{1-6}$alkoxy, and mono or di($C_{1-6}$)alkylamino; and

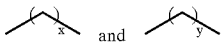

independently represent straight or branched carbon chains which may be substituted with one, two or three substituents independently selected from the group consisting of hydroxy, halogen, cyano, nitro, amino, mono or di($C_{1-6}$)alkylamino, $C_{1-6}$alkyl, $C_{2-6}$alkenyl, $C_{2-6}$alkynyl, $C_{3-7}$cycloalkyl, $C_{1-6}$alkoxy, $C_{1-6}$haloalkyl, and $C_{1-6}$haloalkoxy;
x is 0, 1, 2, or 3; and
y is 0, 1, 2, or 3.

Such compounds are referred to hereinafter as compounds of Formula II.

Preferred $R_1$ and $R_2$ groups for compounds of Formula II include hydrogen, methyl, and ethyl with hydrogen being particularly preferred. In compounds of Formula II $R_3$ is preferably hydrogen or methyl, and Ar is preferably phenyl, pyrimidinyl, pyridizinyl, pyridyl, or pyrazolyl, more preferably Ar is phenyl, pyridyl, or pyridizinyl.

Other particular compounds embraced within the invention include those of general formula I where
n is 0, 1, or 2;
$R_1$ and $R_2$ are independently selected from hydrogen, halogen, hydroxy, alkyl, alkenyl, alkynyl, alkoxy, haloalkyl, haloalkoxy, nitro, cyano, amino, mono- or dialkylamino;
$R_3$ is hydrogen or $C_{1-6}$ alkyl;
Ar is aryl or a saturated, unsaturated, or aromatic heterocyclic group, wherein each aryl of heterocyclic group is optionally substituted with 1, 2, 3, or 4 substituents independently selected from the group consisting of halogen, cyano, hydroxy, nitro, azido, alkanoyl, amino, mono or dialkylamino, haloalkoxy, carboxamido, alkyl, alkenyl, alkynyl, alkoxy, cycloalkyl, cycloalkylalkyl, haloalkyl, haloalkenyl, haloalkynyl, aryloxy, alkylthio, alkylsulfinyl, alkylsulfonyl, aminoalkyl, aryl, arylalkyl, arylalkoxy, heteroaryl heterocycloalkyl;

when n is 0 or 2, Ar is optionally substituted with G where G represents a group of the formula:

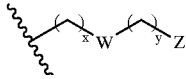

where

W is oxygen, NH, N-alkyl, N-acyl, sulfur, or $CR_5R_6$ where $R_5$ and $R_6$ are the same or different and represent hydrogen, alkyl, or $R_5$ and $R_6$ may be taken together to form a saturated or partially unsaturated carbocyclic ring having 3–7 carbon atoms;

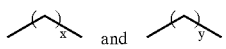

independently represent straight or branched carbon chains which may be substituted with one, two or three substituents independently selected from the group consisting of halogen, hydroxy, cyano, nitro, amino, mono or dialkylamino, alkyl, alkenyl, alkynyl, cycloalkyl, alkoxy, haloalkyl, and haloalkoxy;

x is 0, 1, 2, or 3; and y is 0, 1, 2, or 3; and

Z is hydrogen, hydroxy, alkoxy, cycloalkyl, cycloalkyl (alkoxy), amino, mono or dialkylamino, or —$NR_7COR_8$ where $R_7$ and $R_8$ are the same or different and represent hydrogen or alkyl, or $R_7$ and $R_8$ and the atoms to which they are attached form a heterocycloalkyl ring, or Z is aryl or a saturated, partially unsaturated, or aromatic heterocyclic group of from 1 to 3 rings, 5 to 8 ring members in each ring and, in at least one of said rings, from 1 to about 3 heteroatoms selected from the group consisting of N, O, and S, wherein each aryl or heterocyclic group optionally substituted on each ring with 1, 2, 3, or 4 substituents independently selected from the group consisting of halogen, cyano, hydroxy, nitro, azido, alkanoyl, carboxamido, alkyl, alkenyl, alkynyl, alkoxy, aryloxy, alkylthio, alkylsulfinyl, alkylsulfonyl, aminoalkyl, aryl, haloalkoxy, amino, mono or dialkylamino, cycloalkyl, cycloalkylalkyl, haloalkyl, haloalkenyl, haloalkynyl, arylalkyl, arylalkoxy, heteroaryl, and heterocycloalkyl; or when n is 1, Ar is substituted with at least one group G where G represents

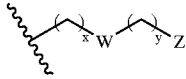

wherein (i) W is sulfur, and

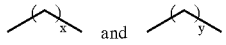

and Z are as defined above;

(ii) W is oxygen, $NR_{10}$ where $R_{10}$ is hydrogen, alkyl, or acyl, or W is $CR_5R_6$ where $R_5$ and $R_6$ are the same or different and represent hydrogen, alkyl, wherein:

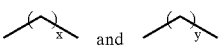

and independently represent straight or branched carbon chains which may be substituted with one, two or three substituents independently selected from the group consisting of halogen, hydroxy, cyano, nitro, amino, mono or dialkylamino, alkyl, alkenyl, alkynyl, cycloalkyl, alkoxy, haloalkyl, and haloalkoxy;

x is 0, 1, 2, or 3; and y is 1, 2, or 3; and

Z is hydroxy, alkoxy, cycloalkyl, cycloalkyl (alkoxy), amino, mono or dialkylamino, or —$NR_7COR_8$ where $R_7$ and $R_8$ are the same or different and represent hydrogen or alkyl, or $R_7$ and $R_8$ and the atoms to which they are attached form a heterocycloalkyl ring, or Z is aryl or a saturated, partially unsaturated, or aromatic heterocyclic group of from 1 to 3 rings, 5 to 8 ring members in each ring and, in at least one of said rings, from 1 to about 3 heteroatoms selected from the group consisting of N, O, and S, wherein each aryl or heterocyclic group optionally substituted on each ring with 1, 2, 3, or 4 substituents independently selected from the group consisting of halogen, cyano, hydroxy, nitro, azido, alkanoyl, carboxamido, alkyl, alkenyl, alkynyl, alkoxy, aryloxy, alkylthio, alkylsulfinyl, alkylsulfonyl, aminoalkyl, aryl, haloalkoxy, amino, mono or dialkylamino, cycloalkyl, cycloalkylalkyl, haloalkyl, haloalkenyl, haloalkynyl, arylalkyl, arylalkoxy, heteroaryl, and heterocycloalkyl;

(iii) W is $CR_5R_6$ where $R_5$ and $R_6$ are taken together to form a saturated or partially unsaturated carbocyclic ring, wherein

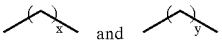

independently represent straight or branched carbon chains which may be substituted with one, two or three substituents independently selected from the group consisting of halogen, hydroxy, cyano, nitro, amino, mono or dialkylamino, alkyl, alkenyl, alkynyl, cycloalkyl, alkoxy, haloalkyl, and haloalkoxy;

x is 1, 2, or 3; and y is 0, 1, 2, or 3; and

Z is hydrogen, hydroxy, alkoxy, cycloalkyl, cycloalkyl (alkoxy), amino, mono or dialkylamino, or —$NR_7COR_8$ where $R_7$ and $R_8$ are the same or different and represent hydrogen or alkyl, or $R_7$ and $R_8$ and the atoms to which they are attached form a heterocycloalkyl ring, or Z is aryl or a saturated, partially unsaturated, or aromatic heterocyclic group of from 1 to 3 rings, 5 to 8 ring members in each ring and, in at least one of said rings, from 1 to about 3 heteroatoms selected from the group consisting of N, O, and S, wherein each aryl or heterocyclic group optionally substituted on each ring with 1, 2, 3, or 4 substituents independently selected from the group consisting of halogen, cyano, hydroxy, nitro, azido, alkanoyl, carboxamido, alkyl, alkenyl, alkynyl, alkoxy, aryloxy, alkylthio, alkylsulfinyl, alkylsulfonyl, aminoalkyl, aryl, haloalkoxy, amino, mono or dialkylamino, cycloalkyl, cycloalkylalkyl, haloalkyl, haloalkenyl, haloalkynyl, arylalkyl, arylalkoxy, heteroaryl, and heterocycloalkyl.

This group of compounds is hereinafter referred to as compounds of Formula III.

Preferred compounds of Formula III include those wherein n is 1;

Ar is phenyl, pyrrolyl, furanyl, pyrazolyl, imidazolyl, pyridyl, pyrimidinyl, pyrazinyl, pyridizinyl, naphthyl, indolyl, quinolinyl, or isoquinolinyl, each of which is substituted with at least one group G and optionally mono-, di-, or trisubstituted with substituents independently chosen from halogen, cyano, nitro, $C_{1-6}$haloalkoxy, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl $(C_{1-3})$alkyl, halo$(C_{1-3})$ alkyl, halo$(C_{2-3})$alkenyl, halo$(C_{2-3})$alkynyl, $C_{1-6}$ alkoxy, and mono or di$(C_{1-6})$alkylamino;

wherein G represents

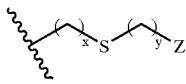

where

Z is hydrogen, hydroxy, alkoxy, cycloalkyl, cycloalkyl (alkoxy), amino, mono or dialkylamino, or —NR$_7$COR$_8$ where R$_7$ and R$_8$ are the same or different and represent hydrogen or alkyl, or Z is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, quinoxalinyl, morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{2-6}$alkenyl, $C_{2-6}$alkynyl, $C_{3-7}$cycloalkyl, $C_{3-7}$ cycloalkyl$(C_{1-3})$alkyl, $C_{1-3}$haloalkoxy, halo$(C_{1-3})$ alkyl, halo$(C_{2-3})$alkenyl, halo$(C_{2-3})$alkynyl, $C_{1-6}$alkoxy, and mono or di$(C_{1-6})$alkylamino; and

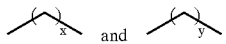

independently represent straight or branched carbon chains which may be substituted with one, two or three substituents independently selected from the group consisting of hydroxy, halogen, cyano, nitro, amino, mono or di$(C_{1-6})$alkylamino, $C_{1-6}$alkyl, $C_{2-6}$alkenyl, $C_{2-6}$alkynyl, $C_{3-7}$cycloalkyl, $C_{1-6}$alkoxy, $C_{1-6}$haloalkyl, and $C_{1-6}$haloalkoxy;

x is 0, 1, 2, or 3; and y is 0, 1, 2, or 3

(hereinafter compounds of Formula III-A)

Preferred compounds of Formula III-A include those where

Ar is phenyl, pyridyl, pyrimidinyl, pyridizinyl or pyrazolyl, each of which is substituted with at least one group G and optionally mono-, di-, or trisubstituted with substituents independently chosen from halogen, cyano, nitro, hydroxy, amino, $C_{1-6}$alkyl, $C_{2-6}$alkenyl, $C_{2-6}$ alkynyl, $C_{3-7}$cycloalkyl, $C_{3-7}$cycloalkyl $(C_{1-3})$ alkyl, halo$(C_{1-3})$ alkyl, halo $(C_{1-3})$ alkoxy, halo $(C_{2-3})$ alkenyl, halo $(C_{2-3})$ alkynyl, $C_{1-6}$ alkoxy, and mono or di$(C_{1-6})$alkylamino;

Z is hydrogen, hydroxy, $C_{1-6}$alkoxy, $C_{3-7}$cycloalkyl, $C_{3-7}$cycloalkyl$(C_{1-3}$alkoxy), amino, mono or di$(C_{1-6})$ alkylamino, or —NR$_7$COR$_8$ where R$_7$ and R$_8$ are the same or different and represent hydrogen or $C_{1-6}$alkyl, or Z is morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{3-7}$ cycloalkyl, $C_{3-7}$ cycloalkyl$(C_{1-3})$alkyl, halo$(C_{1-3})$alkyl, halo $(C_{1-3})$ alkoxy, $C_{1-6}$ alkoxy, or mono and di$(C_{1-6})$alkylamino; and

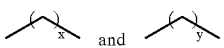

independently represent methylene groups; where x is 0, 1, 2, or 3; and y is 0, 1, 2, or 3.

Other preferred compounds of Formula III-A are those where x is 0.

Yet other preferred compounds of Formula III-A are those where

Z is hydrogen, hydroxy, $C_{1-6}$ alkoxy, $C_{3-7}$cycloalkyl$(C_{1-3}$alkoxy), amino, or mono or di$(C_{1-6})$alkylamino, or Z is morpholinyl, pyrrolidinyl, piperidinyl, or piperazinyl, each of which is optionally mono-, di-, or trisubstituted independently with substituents independently chosen from halogen, amino, cyano, nitro, $C_{1-6}$haloalkyl, $C_{1-6}$haloalkyoxy, hydroxy, $C_{1-6}$alkyl, $C_{3-7}$cycloalkyl, $C_{3-7}$cycloalkyl$(C_{1-3})$alkyl, halo$(C_{1-3})$alkyl, halo $(C_{1-3})$ alkoxy, $C_{1-6}$ alkoxy, and mono or di$(C_{1-6})$alkylamino.

Still more preferred compounds of Formula III-A are those where

Z is amino, mono or di$(C_{1-6})$alkylamino, or

Z is morpholinyl, pyrrolidinyl, piperidinyl, or piperazinyl, each of which is optionally mono- or disubstituted with substituents independently chosen from halogen, amino, cyano, nitro, $C_{1-2}$haloalkyl, $C_{1-2}$haloalkoxy, hydroxy, $C_{1-6}$ alkyl, $C_{1-6}$ alkoxy or mono or di$(C_{1-6})$alkylamino.

More preferred compounds of Formula III include those where n is 1;

Ar is phenyl, pyrrolyl, furanyl, pyrazolyl, imidazolyl, pyridyl, pyrimidyl, pyrazinyl, naphthyl, indolyl, quinolinyl, isoquinolinyl, pyrazolyl, or pyridizinyl, each of which is substituted with at least one group G and optionally mono-, di-, or trisubstituted with halogen, cyano, nitro, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl$(C_{1-3})$alkyl, halo$(C_{1-3})$alkyl, halo$(C_{1-3})$alkoxy, halo$(C_{2-3})$alkenyl, halo $(C_{2-3})$alkynyl, $C_{1-6}$ alkoxy, or mono or di$(C_{1-6})$ alkylamino;

wherein G represents

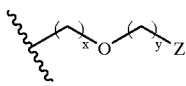

where

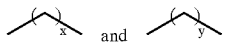

independently represent straight or branched carbon chains which may be substituted with one, two or three substituents independently selected from the group consisting of hydroxy, halogen, cyano, nitro, amino, mono or di($C_{1-6}$)alkylamino, $C_{1-6}$alkyl $C_{2-6}$alkenyl, $C_{3-7}$cycloalkyl, $C_{1-6}$alkoxy, $C_{1-6}$haloalkyl, and $C_{1-6}$haloalkoxy;

x is 0, 1, or 2;

y is 1, 2, or 3; and

Z is hydroxy, $C_{1-6}$alkoxy, $C_{3-7}$cycloalkyl ($C_{1-3}$alkoxy), amino, mono or di($C_{1-6}$)alkylamino, or —$NR_7COR_8$ where $R_7$ and $R_8$ are the same or different and represent hydrogen or $C_{1-6}$alkyl, or Z is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, quinoxalinyl, morpholinyl, pyrrolidinyl, piperidinyl, pyridizinyl, or piperazinyl, each of which is optionally mono-, di-, or trisubstituted with substituents independently chosen from halogen, amino, cyano, nitro, hydroxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkyl, halo($C_{1-3}$)alkoxy, halo($C_{2-3}$)alkenyl, halo($C_{2-3}$)alkynyl, $C_{1-6}$ alkoxy, and mono or di($C_{1-6}$)alkylamino (hereinafter referred to as compounds of Formula III-B).

Preferred compounds of Formula III-B include those where

Ar is phenyl, pyridyl, pyrimidinyl, pyridizinyl or pyrazolyl, each of which is substituted with at least one group G and optionally mono-, di-, or trisubstituted with substituents independently chosen from halogen, cyano, nitro, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$) alkoxy, halo($C_{1-3}$)alkyl, halo($C_{2-3}$)alkenyl, halo($C_{2-3}$) alkynyl, $C_{1-6}$ alkoxy, and mono or di($C_{1-6}$)alkylamino;

Z is hydroxy, alkoxy, cycloalkyl(alkoxy), amino, mono- or di($C_1$–$C_6$)alkylamino, or —$NR_7COR_8$ where $R_7$ and $R_8$ are the same or different and represent hydrogen or $C_1$–$C_6$ alkyl, or Z is morpholinyl, pyrrolidinyl, piperidinyl, or piperazinyl, each of which is optionally mono-, di-, or trisubstituted with substituents independently chosen from halogen, amino, cyano, nitro, trifluoromethyl, trifluoromethoxy, hydroxy, $C_{1-6}$ alkyl, $C_{3-7}$ cycloalkyl, $C_{3-7}$ cycloalkyl ($C_{1-3}$)alkyl, halo($C_{1-3}$)alkyl, $C_{1-6}$ alkoxy, and mono or di($C_{1-6}$)alkylamino; and

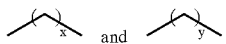

independently represent methylene groups; where x is 0, 1, 2, or 3; and y is 1, 2, or 3.

More preferred compounds of Formula III-B are those wherein x is 0.

Still other more preferred compounds of Formula III-B are those where

Z is hydroxy, $C_1$–$C_6$ alkoxy, $C_3$–$C_7$ cycloalkyl($C_1$–$C_6$) alkoxy, amino, or mono- or di($C_1$–$C_6$)alkylamino, or Z is morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{3-7}$ cycloalkyl, $C_{3-7}$ cycloalkyl($C_{1-3}$)alkyl, halo($C_{1-3}$)alkyl, halo($C_{1-3}$) alkoxy, $C_{1-6}$ alkoxy, and mono or di($C_{1-6}$)alkylamino.

Further more preferred compounds of Formula III-B are those where y is 1, 2, or 3;

Z is amino, or mono- or di($C_1$–$C_4$)alkylamino, or

Z is morpholinyl, pyrrolidinyl, piperidinyl, or piperazinyl, each of which is optionally mono- or disubstituted independently with $C_{1-6}$ alkyl, or mono or di($C_{1-6}$)alkylamino.

Particularly preferred compounds of Formula III-B are those where

Z is amino, mono or di($C_1$–$C_6$)alkylamino, or

Z is morpholinyl, pyrrolidinyl, piperidinyl, or piperazinyl, each of which is optionally mono- or disubstituted independently with $C_{3-7}$ cycloalkyl, $C_{3-7}$ cycloalkyl($C_{1-3}$) alkyl, or $C_{1-6}$ alkyl.

Other particularly preferred compounds of Formula III-B are those where Z is mono or di($C_1$–$C_3$)alkylamino.

Still other particularly preferred compounds of Formula III-B are those where y is 1, 2, or 3 and Z is $C_1$–$C_3$ alkylamino.

Yet other particularly preferred compounds of Formula III-B are those where $R_1$ and $R_2$ are independently selected from hydrogen, halogen, hydroxy, $C_{1-6}$ alkyl, $C_{2-6}$ alkenyl, $C_{2-6}$ alkynyl, $C_{1-6}$ alkoxy, $C_{1-2}$haloalkyl, $C_{1-2}$haloalkoxy, nitro, cyano, amino, and mono- and di($C_{1-6}$)alkylamino.

Other particularly preferred compounds of Formula III-B are those where $R_1$ and $R_2$ are independently selected from the group consisting of hydrogen, halogen, hydroxy, $C_{1-2}$ alkyl, $C_{1-2}$alkoxy, $C_{1-2}$haloalkyl, and $C_{1-2}$haloalkoxy.

Other more preferred compounds of Formula III include those where n is 1;

Ar is phenyl, pyrrolyl, furanyl, pyrazolyl, imidazolyl, pyridyl, pyrimidyl, pyrazinyl, naphthyl, indolyl, quinolinyl, pyrazolyl, pyridizinyl, or isoquinolinyl, each of which is substituted with at least one group G and optionally mono-, di-, or trisubstituted with substituents independently chosen from halogen, cyano, nitro, hydroxy, amino, $C_{1-6}$ alkyl, $C_{2-6}$ alkenyl, $C_{2-6}$ alkynyl, $C_{3-7}$ cycloalkyl, $C_{3-7}$cycloalkyl($C_{1-3}$)alkyl, halo($C_{1-3}$) alkyl, halo($C_{1-3}$)alkoxy, halo($C_{2-3}$)alkenyl, halo($C_{2-3}$) alkynyl, $C_{1-6}$ alkoxy, and mono or di($C_{1-6}$)alkylamino;

wherein G represents

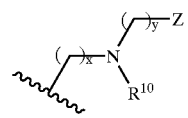

where $R_{10}$ is hydrogen, $C_{1-6}$ alkyl, or $C_{2-6}$ acyl;

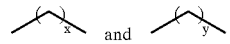

independently represent straight or branched carbon chains which may be substituted with one, two or three substituents independently selected from the group consisting of hydroxy, halogen, cyano, nitro, amino, mono or di($C_{1-6}$)alkylamino, $C_{1-6}$alkyl, $C_{2-6}$alkenyl, $C_{3-7}$cycloalkyl, $C_{1-6}$alkoxy, $C_{1-6}$haloalkyl, and $C_{1-6}$haloalkoxy;
x is 0, 1, or 2;
y is 1, 2, or 3; and
Z is hydroxy, alkoxy, $C_{3-7}$cycloalkyl ($C_{1-3}$alkoxy), amino, mono or di($C_{1-6}$)alkylamino, or —NR$_7$COR$_8$ where R$_7$ and R$_8$ are the same or different and represent hydrogen or $C_{1-6}$alkyl, or
Z is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, quinoxalinyl, morpholinyl, pyrrolidinyl, piperidinyl, pyridizinyl, or piperazinyl, each of which is optionally mono-, di-, or trisubstituted with substituents independently chosen from halogen, amino, cyano, nitro, hydroxy, $C_{1-6}$ alkyl, $C_{2-6}$alkenyl, $C_{2-6}$ alkynyl, $C_{3-7}$ cycloalkyl, $C_{3-7}$ cycloalkyl($C_{1-3}$)alkyl, halo($C_{1-3}$) alkyl, halo($C_{1-3}$)alkoxy, halo($C_{2-3}$)alkenyl, halo ($C_{2-3}$)alkynyl, $C_{1-6}$ alkoxy, and mono or di($C_{1-6}$) alkylamino.

(hereinafter referred to as compounds of Formula III-C).

Preferred compounds of Formula III-C are those wherein:
$R_{10}$ is hydrogen or $C_1$–$C_6$ alkyl;
Ar is phenyl, pyridyl, pyrimidinyl, pyridizinyl or pyrazolyl, each of which is substituted with at least one group G and optionally mono-, di-, or trisubstituted with substituents independently chosen from halogen, cyano, nitro, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$) alkoxy, halo($C_{1-3}$)alkyl, halo ($C_{2-3}$) alkenyl, halo($C_{2-3}$) alkynyl, $C_{1-6}$ alkoxy, and mono or di($C_{1-6}$)alkylamino;
Z is hydroxy, alkoxy, cycloalkyl(alkoxy), amino, mono- or di($C_1$–$C_6$)alkylamino, or —NR$_7$COR$_8$ where R$_7$ and R$_8$ are the same or different and represent hydrogen or $C_1$–$C_6$ alkyl, or
Z is morpholinyl, pyrrolidinyl, piperidinyl, or piperazinyl, each of which is optionally mono-, di-, or trisubstituted with substituents independently chosen from halogen, amino, cyano, nitro, trifluoromethyl, trifluoromethoxy, hydroxy, $C_{1-6}$ alkyl, $C_{3-7}$ cycloalkyl, $C_{3-7}$ cycloalkyl ($C_{1-3}$)alkyl, halo($C_{1-3}$)alkyl, $C_{1-6}$ alkoxy, and mono or di($C_{1-6}$)alkylamino; and

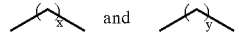

independently represent methylene groups; where
x is 0, 1, 2, or 3; and
y is 1, 2, or 3.

More preferred compounds of Formula III-C are those wherein x is 0 and $R_{10}$ is hydrogen or methyl.

Still other more preferred compounds of Formula III-C are those where
Z is hydroxy, $C_1$–$C_6$ alkoxy, $C_3$–$C_7$ cycloalkyl($C_1$–$C_6$) alkoxy, amino, or mono- or di($C_1$–$C_6$)alkylamino, or
Z is morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{3-7}$ cycloalkyl, $C_{3-7}$ cycloalkyl($C_{1-3}$)alkyl, halo ($C_{1-3}$)alkyl, halo ($C_{1-3}$) alkoxy, $C_{1-6}$ alkoxy, and mono or di($C_{1-6}$)alkylamino.

Further more preferred compounds of Formula III-C are those where
y is 1, 2, or 3;
Z is amino, or mono- or di($C_1$–$C_4$)alkylamino, or
Z is morpholinyl, pyrrolidinyl, piperidinyl, or piperazinyl, each of which is optionally mono- or disubstituted independently with $C_{1-6}$ alkyl, or mono or di($C_{1-6}$)alkylamino.

Particularly preferred compounds of Formula III-C are those where
Z is amino, mono or di($C_1$–$C_6$)alkylamino, or
Z is morpholinyl, pyrrolidinyl, piperidinyl, or piperazinyl, each of which is optionally mono- or disubstituted independently with $C_{3-7}$ cycloalkyl, $C_{3-7}$ cycloalkyl($C_{1-3}$) alkyl, or $C_{1-6}$ alkyl.

Other particularly preferred compounds of Formula III-C are those where Z is mono or di($C_1$–$C_3$)alkylamino.

Still other particularly preferred compounds of Formula III-C are those where y is 1, 2, or 3 and Z is $C_1$–$C_2$ alkylamino.

Yet other particularly preferred compounds of Formula III-C are those where $R_1$ and $R_2$ are independently selected from hydrogen, halogen, hydroxy, $C_{1-6}$ alkyl, $C_{2-6}$ alkenyl, $C_{2-6}$ alkynyl, $C_{1-6}$ alkoxy, $C_{1-2}$haloalkyl, $C_{1-2}$haloalkoxy, nitro, cyano, amino, and mono- and di($C_{1-6}$)alkylamino.

Other particularly preferred compounds of Formula III-C are those where $R_1$ and $R_2$ are independently selected from the group consisting of hydrogen, halogen, hydroxy, $C_{1-2}$ alkyl, $C_{1-2}$ alkoxy, $C_{1-2}$haloalkyl, and $C_{1-2}$haloalkoxy.

Preferred compounds of Formulae I, II and III are those where $R_3$ is hydrogen.

Another particular group of compounds is those of Formula IV, i.e., compounds of general formula I where
n is 0 or 2;
$R_1$ and $R_2$ are independently selected from the group consisting of hydrogen, halogen, hydroxy, $C_{1-2}$ alkyl, $C_{1-2}$ alkoxy, $C_{1-2}$haloalkyl, and $C_{1-2}$haloalkoxy;
Ar is phenyl, pyrrolyl, furanyl, pyrazolyl, imidazolyl, pyridyl, pyrimidinyl, pyrazinyl, pyridizinyl, naphthyl, indolyl, quinolinyl, or isoquinolinyl, each of which is optionally mono-, di-, or trisubstituted with substituents independently chosen from halogen, cyano, nitro, $C_{1-6}$haloalkyl, $C_{1-6}$haloalkoxy, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkyl, halo($C_{2-3}$)alkenyl, halo($C_{2-3}$)alkynyl, $C_{1-6}$ alkoxy, mono or di($C_{1-6}$) alkylamino and G; wherein
G represents

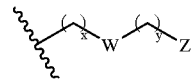

where
W is nitrogen, oxygen, or CR$_5$R$_6$ where R$_5$ and R$_6$ are the same or different and represent hydrogen or straight or branched chain $C_{1-6}$ alkyl;
Z is selected from the group consisting of hydrogen, hydroxy, $C_{1-6}$alkoxy, $C_{3-7}$cycloalkyl, $C_{3-7}$cycloalkyl ($C_{1-3}$alkoxy) amino, and mono or di($C_{1-6}$) alkylamino; or
Z is piperidinyl, piperazinyl, pyrrolidinyl, morpholinyl, phenyl, pyridyl, pyrazolyl, pyrimidinyl, or pyridizinyl, each of which is optionally substituted with one, two, or three groups independently selected from the group consisting of halo($C_1$–$C_6$)

alkyl, halo($C_1$–$C_6$)alkoxy, halogen, $C_{1-6}$ alkyl, hydroxy, and $C_{1-6}$ alkoxy;

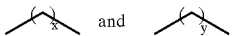

represent straight or branched carbon chains which may be substituted with one, two or three substituents independently selected from the group consisting of hydroxy, halogen, amino, mono or di($C_{1-6}$) alkylamino, $C_{1-6}$alkyl, $C_{2-6}$alkenyl, $C_{2-6}$alkynyl, $C_{3-7}$cycloalkyl, $C_{1-6}$alkoxy, $C_{1-6}$haloalkyl, and $C_{1-6}$haloalkoxy;

x is 0, 1, 2, or 3; and y is 0, 1, 2, or 3.

Preferred compounds of Formula IV are those where Ar is phenyl, pyrazolyl, pyridyl, pyrimidinyl, or pyridizinyl, each of which is optionally mono-, di-, or trisubstituted with substituents independently chosen from halogen, cyano, nitro, $C_{1-6}$haloalkyl, $C_{1-6}$haloalkoxy, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkyl, halo($C_{2-3}$)alkenyl, halo($C_{2-3}$)alkynyl, $C_{1-6}$ alkoxy, mono or di($C_{1-6}$)alkylamino and G.

More preferred compounds of Formula IV are those where Ar is phenyl, pyrazolyl, pyridyl, pyrimidinyl, or pyridizinyl, each of which is substituted with at least one G and optionally substituted with one or two groups independently selected from halogen, $C_1$–$C_6$ alkyl, $C_1$–$C_6$ alkoxy, trifluoromethyl, amino, and mono- and di($C_1$–$C_6$) alkylamino.

Preferred compounds of Formulae III-B and III-C include those where $R_1$ and $R_2$ are independently selected at each occurrence from hydrogen, methyl and ethyl.

Particularly preferred compounds of Formulae III-B and III-C are those where no more than three of $R_1$ and $R_2$ are other than hydrogen.

Other particularly preferred compounds of Formulae III-B and III-C include those where one, two, or three of $R_1$ and $R_2$ is methyl or ethyl, and the remaining $R_1$ and $R_2$ substituents are hydrogen.

Particularly preferred compounds of Formulae III-A are those where one, two, or three of $R_1$ and $R_2$ is methyl or ethyl, and the remaining $R_1$ and $R_2$ substituents are hydrogen.

Other particularly preferred compounds of Formula III-A are those where Ar is phenyl, pyridizinyl, or pyridyl, each of which is a) substituted with one group selected from halogen, $C_1$–$C_3$ alkyl, $C_1$–$C_3$ alkoxy, nitro, amino, and mono- and di($C_1$–$C_2$)alkylamino; and b) substituted with $C_1$–$C_3$ alkoxy substituted with: $C_1$–$C_3$ alkylamino, di ($C_1$–$C_3$) alkylamino, amino, morpholino, piperazinyl, 4-($C_{1-4}$) alkylpiperazinyl, piperidinyl or piperidinyl optionally substituted with $C_1$–$C_4$ alkyl.

Particularly preferred compounds of Formula III-B and Formula III-C are those where phenyl, pyridyl, or pyridizinyl, each of which is (a) substituted with one group selected from halogen, $C_1$–$C_3$ alkyl, $C_1$–$C_3$ alkoxy, nitro, amino, and mono- and di($C_1$–$C_2$)alkylamino; and (b) substituted with $C_1$–$C_3$ alkoxy substituted with: $C_1$–$C_3$ alkylamino, di ($C_1$–$C_3$) alkylamino, amino, morpholino, piperazinyl, 4-($C_{1-4}$) alkylpiperazinyl, piperidinyl or piperidinyl optionally substituted with $C_1$–$C_4$ alkyl.

This invention provides aryl substituted tetrahydroindazoles. Preferred examples of the invention bind with high affinity to the benzodiazepine site of $GABA_A$ receptors, including human $GABA_A$ receptors. Particularly preferred compounds are those that bind with high selectivity to the benzodiazepine site of $GABA_A$ receptors, including human $GABA_A$ receptors. Without wishing to be bound to any particular theory, it is believed that the interaction of the compounds of Formula I with the benzodiazepine site results in the pharmaceutical utility of these compounds.

The invention further comprises methods of treating patients in need of such treatment with an amount of a compound of the invention sufficient to alter the symptoms of a CNS disorder. Compounds of the invention that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the invention that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder+/−agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g. attention deficit disorder (ADD), and attention deficit and hyperactivity disorder (ADHD).

The invention also provides pharmaceutical compositions comprising compounds of the invention, including packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5\text{-}HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211–218; Smith, et al., *Am. J. Psychiatry* (1998) 155(10) 1339–45; or Le, et al., *Alcohol and Alcoholism* (1996) 31 Suppl. 127–132. Also see, the discussion of the use of the $GABA_A$ receptor ligand 3-(5-methylisoxazol-3-yl)-6-(1-methyl-1,2,3-triazol-4-yl) methyloxy-1,2,4-triazolo [3,4-a]phthalazine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The invention also pertains to methods of inhibiting the binding of benzodiazepine compounds, such as Ro15–1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 8. The $GABA_A$ receptors used to determine in vitro binding may be obtained from a variety of sources, for example from preparations of rat cortex or from cells expressing cloned human $GABA_A$ receptors.

The invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 9.

The $GABA_A$ receptor ligands provided by this invention and labeled derivatives thereof are also useful as standards and reagents in determining the ability of a potential pharmaceutical to bind to the $GABA_A$ receptor.

Labeled derivatives of the $GABA_A$ receptor ligands provided by this invention are also useful as radiotracers for positron emission tomography (PET) imaging or for single photon emission computerized tomography (SPECT).

The compounds herein described may have one or more asymmetric centers. Compounds of the invention containing an asymmetrically substituted atom may be isolated in enantiomerically enhanced or racemic form. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent; derivatizing with an enantiomerically enriched resolving reagent, separating the resulting diastereomers through means well known in the art, and removing the enantiomerically enriched derivatizing agent through ordinary chemical means such as, for example, hydrolysis or hydrogenation; or chromatography, using, for example a chiral HPLC column.

Many geometric isomers of olefins, C=N double bonds, and the like can also be present in the compounds described herein, and all such stable isomers are contemplated in the invention. Cis, trans Z and E geometric isomers of the compounds of the invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

Some compounds of the invention may exist as tautomers. Unless otherwise specified, any description or claim of one tautomeric form is intended to encompass the other tautomer.

The term "substituted", as used herein, means that any one or more hydrogens on the designated atom is replaced with a selection from the indicated group, provided that the designated atom's normal valence is not exceeded, and that the substitution results in a stable compound. When a substituent is keto (i.e., =0), then 2 hydrogens on the atom are replaced. Keto substituents are not present on aromatic moieties. The invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and each R* is selected independently from the definition of R*. Also, combinations of substituents and/or variables are permissible only if such combinations result in stable compounds.

Where the term "alkyl" is used, either alone or within other terms such as "haloalkyl" and "alkylsulfonyl", it embraces linear, i.e., straight, and branched chain groups having one to about twelve carbon atoms. Preferred alkyl groups are "lower alkyl" groups having one to about ten carbon atoms. More preferred are lower alkyl groups having one to about six carbon atoms. Examples of alkyl include, but are not limited to, methyl, ethyl, n-propyl, iso-propyl, n-butyl, sec-butyl, tert-butyl, n-pentyl, and sec-pentyl and the like. Preferred alkyl groups are $C_1$–$C_6$ alkyl groups. Especially preferred alkyl groups are methyl, ethyl, propyl, butyl, 3-pentyl. The term $C_1$–$C_6$ alkyl as used herein includes alkyl groups having from 1 to 6 carbon atoms. Preferred examples are methyl and ethyl.

"Alkylsulfonyl" embraces alkyl groups attached to a sulfonyl group, where alkyl is defined as above, i.e., a group of the formula —$SO_a$(alkyl). More preferred alkylsulfonyl groups are "lower alkylsulfonyl" groups having one to six carbon atoms. Examples of such lower alkylsulfonyl groups include methylsulfonyl, ethylsulfonyl and propylsulfonyl.

The term "alkylsulfinyl" embraces groups containing a linear or branched alkyl group, of one to ten carbon atoms, attached to a divalent —S(=O)— atom.

The terms "N-alkylamino" and "N,N-dialkylamino" denote amino groups which have been substituted with one alkyl group and with two alkyl groups, respectively. More preferred alkylamino groups are "lower alkylamino" groups having one or two alkyl groups of one to six carbon atoms, attached to a nitrogen atom. Suitable "alkylamino" may be mono or dialkylamino such as N-methylamino, N-ethylamino, N,N-dimethylamino, N,N-diethylamino or the like.

The term "alkylthio" embraces groups containing a linear or branched alkyl group, of one to ten carbon atoms, attached to a divalent sulfur atom. An example of "alkylthio" is methylthio, ($CH_3$—S—).

The term "cycloalkyl" embraces groups having three to ten carbon atoms. More preferred cycloalkyl groups are "lower cycloalkyl" groups having three to seven carbon atoms, i.e., $C_3$-$c_7$ cycloalkyl. Examples include groups such as cyclopropyl, cyclobutyl, cyclopentyl, cyclohexyl and cycloheptyl.

In the term "$C_3$–$C_7$ cycloalkylalkyl", the $C_{3-7}$ cycloalkyl group is attached to the parent molecular moiety through the alkyl, preferably a $C_1$–$C_6$, more preferably a $C_1$–$C_4$ alkyl, group. This term encompasses, but is not limited to, cyclopropylmethyl, and cyclohexylmethyl.

By "carboxamido" as used herein is meant groups of the formula —C(O)NR'R" where R' and R" are the same or different and represent hydrogen or alkyl. Preferred carboxamido groups are those where both of R' and R" are hydrogen.

The term "alkenyl" embraces unsaturated straight and branched chain groups having two to about ten carbon atoms. Such groups contain at least one carbon-carbon double bond which may occur at any stable point along the chain. Examples of alkenyl groups include, but are not limited to such groups as ethenyl and propenyl.

The term "alkynyl" embraces straight and branched chain groups having two to about ten carbon atoms and at least one carbon-carbon triple bond. The carbon-carbon triple bond may occur at any stable point along the chain. Examples of alkynyl groups include, but are not limited to such groups as ethynyl and propynyl.

"Alkoxy" represents an alkyl group as defined above attached to the parent molecular moiety through an oxygen bridge. Examples of alkoxy include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, and 3-methylpentoxy. More preferred alkoxy groups include methoxy, ethoxy, isopropoxy, and isobutoxy.

As used herein, "alkanoyl" and "acyl" refer to an alkyl group as defined above attached through a carbonyl bridge, i.e., —CO(alkyl). Examples include acetyl, propionyl, and butyryl.

The term "aryl" is used to indicate aromatic groups that contain only carbon atoms in the ring structure. Thus, the term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups are, for example, phenyl, naphthyl, 1,2,3,4-tetrahydronaphthalene, indanyl, and biphenyl. Preferred aryl groups include phenyl, naphthyl, including 1-naphthyl and 2-naphthyl, and acenaphthyl. More preferred aryl groups include phenyl and napthyl. The aryl groups herein are unsubstituted or, as specified, substituted in one or more substitutable positions with various groups. Thus, such aryl groups are optionally substituted with, for example, $C_1$–$C_6$ alkyl, $C_1$–$C_6$ alkoxy, halogen, hydroxy, cyano, nitro, amino, mono- or di-($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino ($C_1$–$C_6$)alkyl, mono- or di($C_1$–$C_6$)alkylamino($C_1$–$C_6$)alkyl.

The term "haloalkyl" is intended to include both branched and straight-chain saturated aliphatic hydrocarbon groups having the specified number of carbon atoms, substituted with 1 or more halogen (for example —$C_vF_w$ where v=1 to 3 and W=1 to (2v+1). Examples of haloalkyl include, but are not limited to, trifluoromethyl, trichloromethyl, pentafluoroethyl, and pentachloroethyl. Preferred haloalkyl groups are halo($C_1$–$C_6$)alkyl groups; particularly preferred are trifluoromethyl, perfluoropropyl, and difluoromethyl.

By "haloalkoxy" as used herein is meant represents a haloalkyl group, as defined above, attached through an oxygen bridge to a parent group. Preferred haloalkoxy groups are halo($C_1$–$C_6$)alkoxy groups. Examples of haloalkoxy groups are trifluoromethoxy, 2,2-difluoroethoxy, 2,2,3-trifluoropropoxy and perfluoroisopropoxy. The term "halogen" indicates fluorine, chlorine, bromine, and iodine.

As used herein, the term "heterocycloalkyl" is intended to mean a stable 5-to 7-membered monocyclic or 7-to 10-membered bicyclic ring system which contains at least one non-aromatic ring wherein said ring consists of carbon atoms and from 1 to 4 heteroatoms independently selected from the group consisting of N, O and S. The heterocycloalkyl ring or heterocycloalkyl bicyclic ring system may be fused to a benzene ring. A nitrogen in the heterocycle may optionally be quaternized. It is preferred that when the total number of S and O atoms in the heterocycloalkyl group exceeds 1, then these heteroatoms are not adjacent to one another. It is also preferred that the total number of S and O atoms in the heterocycloalkyl is not more than 1. Examples of heterocycloalkyl groups include but are not limited to tetrahydroquinolinyl, tetrahydroisoquinolinyl, pyrrolyl, homopiperazinyl, piperazinyl, homopiperidinyl, piperidinyl, tetrahydrofuranyl, morpholinyl, azetidinyl, 2H-pyrrolyl.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will also recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disterate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It may be convenient to formulate these animal feed and drinking water compositions so that the animal ingests an appropriate quantity of the composition during a meal or throughout the course of the day. It may also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention have desirable pharmacological properties that include, but are not limited to, oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

Preparation of Compounds

EXAMPLES

The invention is illustrated further by the following examples for the preparation of particular compounds of the invention, which are not to be construed as limiting the invention in scope or spirit to the specific procedures described in them. Those having skill in the art will recognize that the starting materials may be varied and additional steps employed to produce compounds encompassed by the invention, as demonstrated by the following examples. Those skilled in the art will also recognize that it may be necessary to utilize different solvents or reagents to achieve some of the above transformations. In some cases, protection of reactive functionalities may be necessary to achieve the above transformations. In general, such need for protecting groups, as well as the conditions necessary to attach and remove such groups, will be apparent to those skilled in the art of organic synthesis.

Unless otherwise specified, all reagents and solvents are of standard commercial grade and are used without further purification. The appropriate atmosphere to run the reaction under, for example, air, nitrogen, hydrogen, argon and the like, will be apparent to those skilled in the art.

The pyrazole carboxamides of the invention can generally be prepared according to the procedures outlined in International Application WO 00/40565. The Ar groups of the compounds of this invention can be prepared according to known procedures. See, for example, International Applications WO 97/2624 and WO 01/16103.

A representative preparation of the compounds of Formula I is depicted in Scheme I.

Scheme I

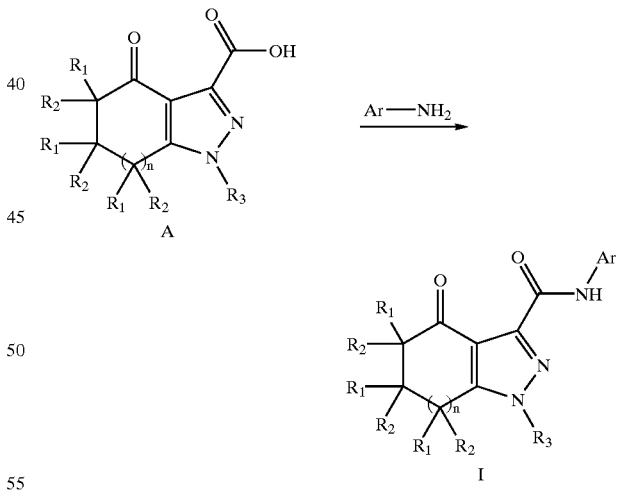

Accordingly, an acid of Formula A is reacted with an amine Ar—$NH_2$ in a mixture of, for example, DMF/DCM in the presence of a coupling agent such as 1-[3-(dimethylamino)propyl]-3-ethylcarbodiimide hydrochloride and a base such as dimethylaminopyridine. Alternatively, an active ester may be prepared from the acid using, for example, Ethyl chloroformate, after which the active ester is reacted with the amine Ar—$NH_2$ in a suitable solvent such as DMF or THF in the presence of base, e.g., triethylamine or dimethylaminopyridine.

The preparation of representative Ar—$NH_2$ groups is depicted below in Schemes II(1), (2) and (3).

Scheme II

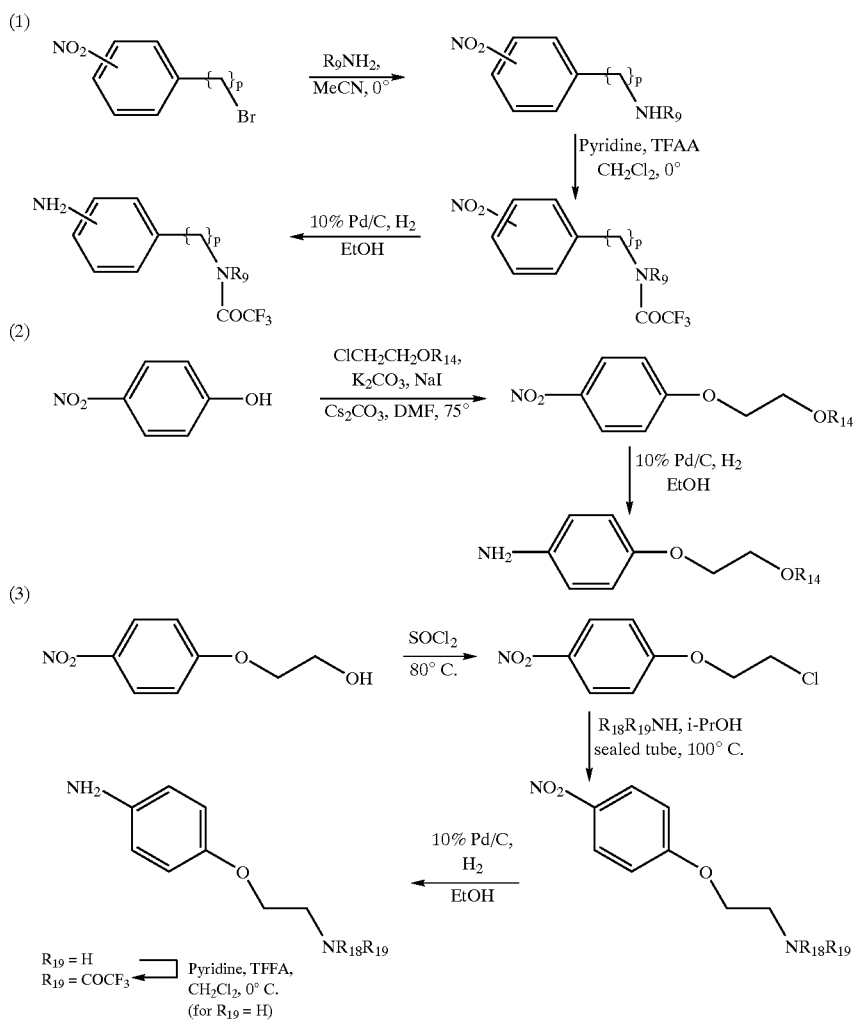

In Schemes II(1) and (2), p is 0 or an integer of from 1–6, $R_9$ and $R_{14}$ represent hydrogen or alkyl, preferably hydrogen or $C_1$–$C_6$ alkyl. In Scheme II(3), $R_{18}$ and $R_{19}$ independently represent hydrogen or alkyl, preferably hydrogen or $C_1$–$C_6$ alkyl, or $NR_{18}R_{19}$ represents a heterocycloalkyl group such as morpholinyl, piperidinyl, or piperazinyl.

A representative preparation of some substituted pyridylamines useful as Ar—$NH_2$ groups for preparing compounds of Formula I as shown in Scheme I is depicted below in Scheme III. In Scheme III, $R_{30}$ represents hydrogen or hydrocarbyl substituted with up to two $R_A$ groups, preferably hydrogen or alkyl substituted with up to two $R_A$ groups.

Scheme III

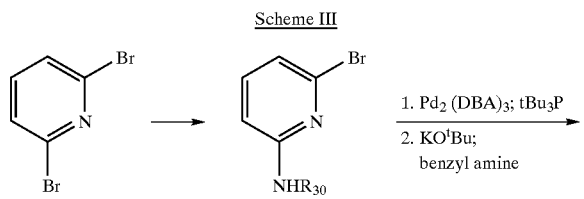

-continued

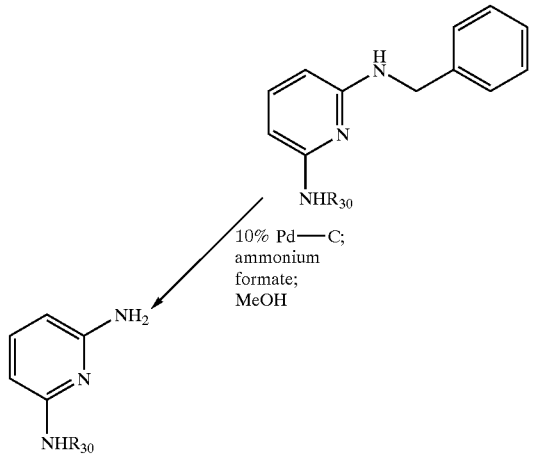

Scheme IV

The preparation of other representative substituted anilines useful as Ar—$NH_2$ groups for preparing compounds of Formula I as shown in Scheme II is depicted below in Scheme IV. In Scheme IV, $R_{35}$ represents hydrogen or $C_1$–$C_6$ alkyl, preferably ethyl.

Scheme IV

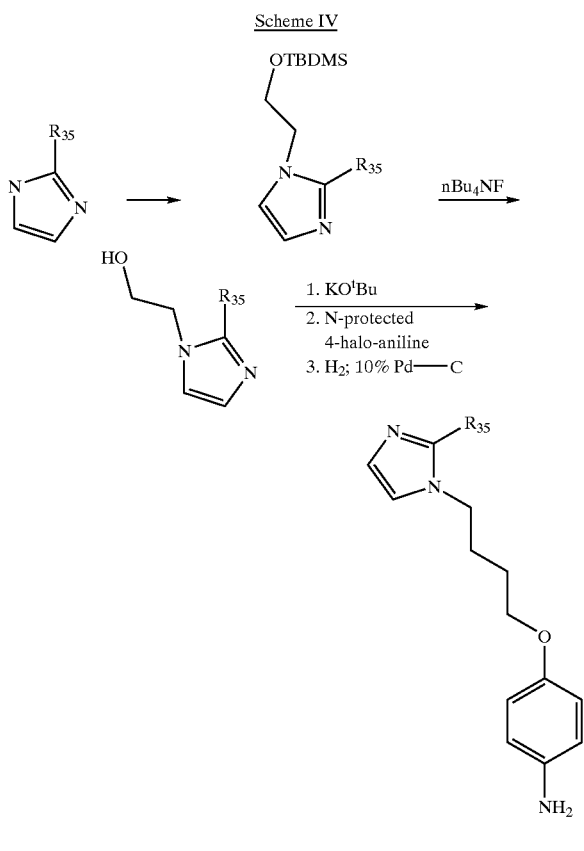

Example 1

Preparation of Starting Materials

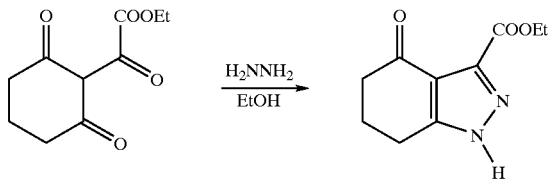

Example 1a

4-Oxo-4,5,6,7,4-tetrahydro-1H-indazole-3-carboxylic acid ethyl ester

A solution of 2-ethyloxalylcyclohexan-1,3-dione (*Synthesis*, 1976, 722) (9.50 g, 45 mmol), hydrazine monohydrate (2.2 mL, 45 mmol), and acetic acid (2.6 mL, 45 mmol) in ethanol (100 mL) is stirred at room temperature for 6 hours. The solvent is evaporated under reduced pressure and the resulting residue is dissolved in acetic acid (100 mL), heated to 120° C. and stirred under nitrogen for 3 hours. The reaction mixture is then cooled to about room temperature and concentrated. The concentrate is dissolved in chloroform (200 mL), treated with 10% NaCl (100 mL), and neutralized with 1 M sodium carbonate. The organic layer is separated, dried over $Na_2SO_4$, filtered and the solvent is evaporated to give 4-oxo-4,5,6,7,4-tetrahydro-1H-indazole-3-carboxylic acid ethyl ester (7.65 g, purity 90%, yield 73%). $^1$H NMR (CDCl$_3$) δ0.95(t, J=7.1 Hz, 3 H), 2.17 (quintet, J=6.4 Hz, 2 H), 2.58 (t, J=6.8 Hz, 2 H), 3.00 (t, J=6.2 Hz, 2 H), 4.44 (q, J=7.3 Hz, 2 H). MW (Calc'd) 208.220; MS (M+H)$^+$209.

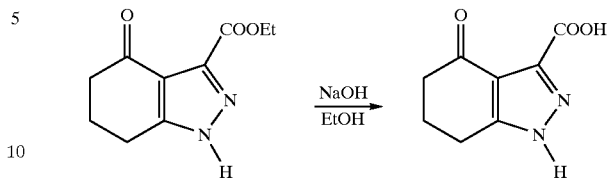

Example 1b

4-Oxo-4,5,6,7,4-tetrahydro-1H-indazole-3-carboxylic acid

A solution of 4-oxo-4,5,6,7–4-tetrahydro-1H-indazole-3-carboxylic acid ethyl ester (purity 90%, 1.84 g, 8.0 mmol) in methanol (20 mL) is treated with 10 N NaOH (4 mL) and stirred under nitrogen at 60° C. for 90 minutes. The reaction mixture is cooled to approximately room temperature and the solvent is evaporated under reduced pressure. The resulting residue is dissolved in water (30 mL), treated with brine (30 mL), and acidified to pH 2 with conc. hydrochloric acid to produce copious precipitate. The mixture is cooled to 0° C., filtered, the solid is washed with water (5 mL), and dried in a vacuum oven to give 4-oxo-4,5,6,7,4-tetrahydro-1H-indazole-3-carboxylic acid (0.99 g, 66%). $^1$H NMR (DMSO-d$_6$) δ2.18 (quintet, J=6.2 Hz, 2 H), 2.66 (t, J=6.4 Hz, 2 H), 2.95 (t, J=6.2 Hz, 2 H).

Example 1c

4-[N-trifluoroacetyl-(methylaminomethyl)aniline

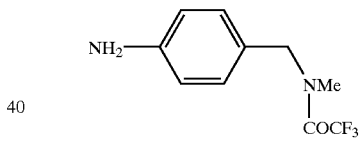

A solution of p-nitrobenzylbromide (5.40 g, 25 mmol) in acetonitrile (60 ml) is added dropwise to a stirred solution of aqueous methylamine (65 mL, 40 wt. %, 0.75 mol) in acetonitrile (50 mL) at 0°. After stirring an additional 15 minutes, the solution is poured into brine and extracted 2× with dichloromethane. The combined organic layers are washed with brine, dried over sodium sulfate, filtered, and concentrated in vacuo to give 4-(methylaminomethyl)nitrobenzene (4.04g).

A solution of trifluoracetic anhydride (4.46 mL, 31.6 mmol) in dichloromethane (10 mL) is added dropwise to a stirred solution of 4-(methylaminomethyl)nitrobenzene (4.04 g, 24.3 mmol) and pyridine (2.16 mL, 26.7 mmol) in dichloromethane (25 mL) at 0°. After stirring an additional 30 minutes, the solution is poured into aqueous 3.6N hydrochloric acid and extracted with dichloromethane. The organic layer is washed with brine, dried over sodium sulfate, filtered, and concentrated in vacuo to give 4-[N-trifluoroacetyl-(methylaminomethyl)]nitrobenzene (6.55 g).

Crude 4-[N-trifluoroacetyl-(methylaminomethyl)]nitrobenzene (6.55 g) is dissolved in ethyl alcohol (75 mL), added to 10% Pd/C (655 mg) in a Parr bottle and shaken under Hydrogen (50 PSI) for 4 hours. The mixture is filtered through Celite and concentrated in vacuo to give 4-[N-trifluoroacetyl-(methylaminomethyl)aniline (5.75 g).

Example 1d

4-amino-(N-trifluoroacetyl-2-methylaminoethoxy)benzene

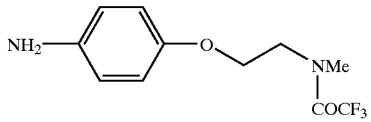

A mixture of p-nitrophenol (1.39 g, 10 mmol), 2-chloroethoxytrimethylsilane (3.2 ml, 20 mmol), potassium carbonate (4.15 g, 30 mmol), cesium carbonate (163 mg, 0.5 mmol), and sodium iodide (149 mg, 1 mmol) in N,N-dimethylformamide (10 ml) is heated at 75° for 19.5 hours. After cooling to ambient temperature, the mixture is diluted with ethyl acetate and filtered. The filtrate is washed with saturated aqueous sodium bicarbonate, then washed 2× with water, dried over magnesium sulfate, filtered, concentrated in vacuo, and purified on Silica gel (1:1 ethyl acetate/hexanes) to give 4-nitro-(2-Hydroxyethoxy)benzene (1.25 g).

4-Nitro-(2-Hydroxyethoxy)benzene (1.13 g, 6.2 mmol) in thionyl chloride (10 mL) is heated at reflux for 3 hours then concentrated in vacuo. After cooling the residue in an ice water bath, saturated aqueous sodium bicarbonate is added and the precipitate collected, rinsed with water, and dried to give 4-nitro-(2-chloroethoxy)benzene (909 mg).

A mixture of 4-nitro-(2-chloroethoxy)benzene (781 mg, 3.9 mmol) and aqueous methylamine (15 mL, 40 wt. %) in isopropyl alcohol (15 mL) is heated in a sealed tube at 100° for 4 hours. After cooling in an ice water bath, the mixtured is poured into brine and extracted 2× with dichloromethane, dried over sodium sulfate, filtered, and concentrated in vacuo to give 4-nitro-(2-methylaminoethoxy)benzene (697 mg).

To a solution of 4-nitro-(2-methylaminoethoxy)benzene (766 mg, 3.9 mmol) and pyridine (0.35 mL, 4.29 mmol) in dichloromethane (5 mL) at 0° C. is added dropwise trifluoroacetic anhydride (0.72 mL, 5.08 mmol). After stirring at 0° C. for 3.5 hours, the mixture is poured into aqueous 1.2 N hydrochloric acid and extracted with dichloromethane. The organic layer is washed with saturated aqueous sodium bicarbonate then brine, dried over sodium sulfate, filtered, and concentrated in vacuo to give 4-nitro-(N-trifluoroacetyl-2-methylaminoethoxy) benzene (1.06 g). Treatment of this nitro compound with 10% Palladium on carbon in ethyl alcohol (18 mL) in a Parr bottle under Hydrogen (55 PSI) for 2.25 hours affords 4-amino-(N-trifluoroacetyl-2-methylaminoethoxy)benzene (709 mg).

Example 2

4-Oxo-4,5,6,7,4-tetrahydro-1H-indazole-3-carboxylic acid 4-[2-(propylamino)ethoxy]phenylamide

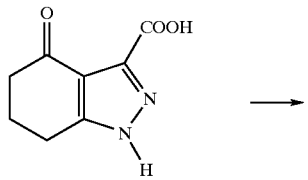

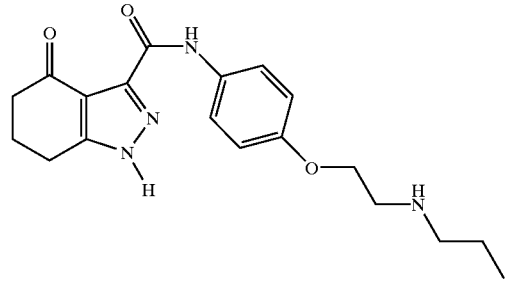

Ethyl chloroformate (0.24 mL, 2.5 mmol) is added to a −5° C. solution of 4-oxo-4,5,6,7-4-tetrahydro-1H-indazole-3-carboxylic acid (180 mg, 1.0 mmol) and triethylamine (0.56 mL, 4.0 mmol) in anhydrous DMF (3.0 mL). After stirring the mixture at 0° C. for 2 hours, [2-(4-Aminophenoxy)-ethyl]-propyl-carbamic acid tert-butyl ester (294 mg, 1.0 mmol) is added. The resulting mixture is stirred at room temperature for 16 hours and then at 50° C. for one hour. Methanol (2 mL) and 4 M KOH (1 mL) are then added, and the stirring at 50° C. is continued for an additional one hour. The reaction mixture is then poured into water (30 mL), neutralized with 1 M HCl, treated with 5% sodium bicarbonate (30 mL), and extracted with ethyl acetate (50 mL). The ethyl acetate layer is washed with water (50 mL), dried over magnesium sulfate, filtered and concentrated under reduced pressure. The residue is dissolved in chloroform (3 mL), treated with trifluoroacetic acid (2 mL), and stirred at room temperature for 3 hours. The reaction mixture is diluted with ethyl acetate (100 mL), washed with 1 M sodium carbonate (100 mL), dried over anhydrous sodium carbonate, filtered and concentrated under reduced pressure. The resulting crude product was purified by silica gel column chromatography using chloroform-methanol-acetic acid (80:16:4, v/v/v) as the eluent to give 95 mg (26%) of 4-oxo-4,5,6,7-tetrahydro-1H-indazole-3-carboxylic acid 4-[2-(propylamino)ethoxy]phenylamide. $^1$H NMR (CDCl$_3$) δ0.95(t, J=7.3 Hz, 3 H), 1.68 (quintet, J=7.5 Hz, 2 H), 2.19 (m, 2 H), 2.65 (m, 2 H), 2.94 (t, J=7.5 Hz, 2 H), 3.00 (m, 2 H), 3.24 (m, 2 H), 4.28 (m, 2 H), 6.50 (bs, 2 H), 6.92 (d, J=9.0 Hz, 2 H), 7.69 (d, J=9.0 Hz, 2 H), 12.3 (s, 1 H). MW (calculated) 356.429; MS (M+H)$^+$357.

Example 3

4-Oxo-4,5,6,7,4-tetrahydro-1H-indazole-3-carboxylic acid [3-fluoro-4-(2-(morpholin-4-yl-ethoxy)phenyl]-amide

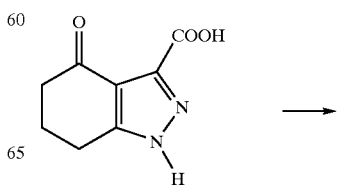

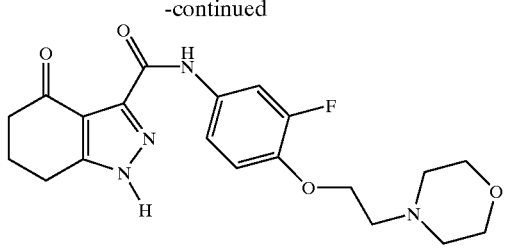

A mixture of 4-oxo-4,5,6,7,4-tetrahydro-1H-indazole-3-carboxylic acid (188 mg, 1.0 mmol), anhydrous DMF (4 mL), anhydrous dichloromethane (8 mL), 1-[3-(dimethylamino)propyl]-3-ethylcarbodiimide hydrochloride (287 mg, 1.5 mmol, DMAP (183 mg, 1.5 mmol), and 3-fluoro-4-(2-morpholin-4-yl-ethoxy)-phenylamine (288 mg, 1.2 mmol) is stirred under nitrogen at room temperature for 3 days. The reaction mixture is poured into 10% NaCl (50 mL) and extracted with chloroform (2×50 mL). The combined chloroform extracts are dried over Na$_2$CO$_3$, filtered and the solvent is evaporated under reduced pressure. The resulting residue is chromatographed on preparative silica gel plates using chloroform-methanol-acetic acid (70:24:6, v/v/v) as the eluent to give 130 mg (32%) of pure 4-oxo-4,5,6,7,4-tetrahydro-1H-indazole-3-carboxylic acid [3-fluoro-4-(2-(morpholin-4-yl-ethoxy)phenyl]-amide, as a white solid. $^1$H NMR (CD$_3$OD) δ2.19 (quintet, J=6.0 Hz, 2 H), 2.65 (m, 6 H), 2.86 (t, J=5.5 Hz, 2 H), 2.95 (t, J=6.2 Hz, 2 H), 3.77 (t, J=4.6 Hz, 4 H), 4.20 (t, J=5.5 Hz, 2 H), 7.01 (t, J=9.0 Hz, 1 H), 7.36 (m, 1 H), 7.83 (dd, J=13.2 and 2.4 Hz, 1 H). MW 402.432 (calculated); MS (M+H)$^+$403.

Example 4

4-Oxo-4,5,6,7-tetrahydro-1H-indazole-3-carboxylic acid [6-(2-propylamino-ethoxy)-pyridin-3-yl]-amide

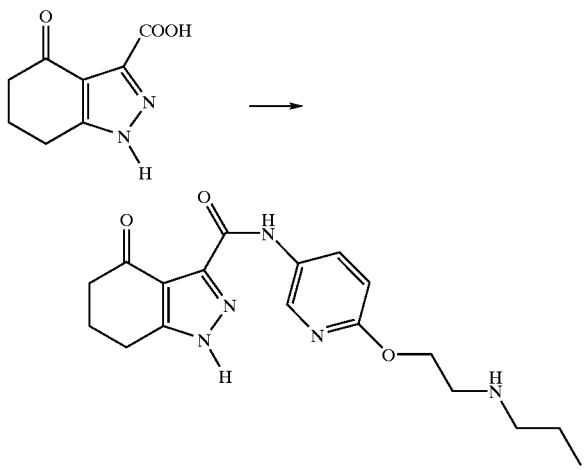

A mixture of 4-oxo-4,5,6,7,4-tetrahydro-1H-indazole-3-carboxylic acid (188 mg, 1.0 mmol), anhydrous DMF (4 mL), anhydrous dichloromethane (8 mL), 1-[3-(dimethylamino)propyl]-3-ethylcarbodiimide hydrochloride (287 mg, 1.5 mmol), DMAP (183 mg, 1.5 mmol), and [2-(5-amino-pyridin-2-yloxy)-ethyl]-propyl-carbamic acid tert-butyl ester (354 mg, 1.2 mmol) is stirred under nitrogen at room temperature for 3 days. The reaction mixture is then poured into 10% aqueous NaCl (50 mL) and extracted with chloroform (2×50 mL). The combined chloroform extracts are dried over Na$_2$CO$_3$, filtered and concentrated to afford a residue. The residue is dissolved in chloroform (10 mL), treated with trifluoroacetic acid (5 mL), and stirred under nitrogen at room temperature for 5 hours. The reaction mixture is evaporated under reduced pressure and the resulting residue is partitioned between chloroform (80 mL) and 1 M Na$_2$CO$_3$ (50 mL). The layers are separated and the chloroform layer is dried over anhydrous Na$_2$CO$_3$, filtered and concentrated. The concentrate was purified by preparative thin layer chromatography using 2000 μm silica gel plates and chloroform-methanol-acetic acid (70:24:6, v/v/v) as the eluent to give 150 mg (42%) of 4-oxo-4,5,6,7-tetrahydro-1H-indazole-3-carboxylic acid [6-(2-propylamino-ethoxy)-pyridin-3-yl]-amide as a white solid. $^1$H NMR (CDCl$_3$) δ0.95 (t, J=7.3 Hz, 3 H), 1.70 (quintet, J=7.7 Hz, 2 H), 2.22 (t, J=6.1 Hz, 2 H), 2.67 (t, J=6.0 Hz, 2 H), 2.92 (t, J=7.5 Hz, 2 H), 3.06 (t, J=6.0 Hz, 2 H), 3.29 (t, J=4.9 Hz, 2 H), 4.51 (t, J=4.8 Hz, 2 H), 6.49 (d, J=8.8 Hz, 1 H), 7.80 (dd, J=8.8 and 2.6 Hz, 1 H), 8.62 (d, J=2.6 Hz, 1 H). MW 357.417 (calculated); MS (M+H)$^+$358, m.p. 120° C.

Example 5

4-Oxo-4,5,6,7-tetrahydro-1H-indazole-3-carboxylic acid [6-(2-ethylamino-ethoxy)-pyridin-3-yl]-amide

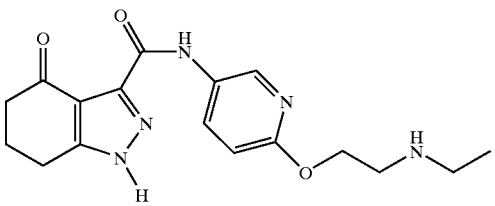

The title compound is obtained from a reaction of 4-oxo-4,5,6,7,4-tetrahydro-1H-indazole-3-carboxylic acid (188 mg, 1.0 mmol) with [2-(5-amino-pyridin-2-yloxy)-ethyl]-ethyl-carbamic acid tert-butyl ester (338 mg, 1.2 mmol) in the presence of 1-[3-(dimethylamino)propyl]-3-ethylcarbodiimide hydrochloride (287 mg, 1.5 mmol) and DMAP (183 mg, 1.5 mmol) using the procedure described above in Example 4. Yield: 120 mg (35%) of the desired product as a white solid. $^1$H NMR (CD$_3$OD) δ1.17 (t, J=7.1 Hz, 3 H), 2.24 (quintet, J=6.4 Hz, 2 H), 2.70 (t, J=6.4 Hz, 2 H), 2.75 (q, J=7.0 Hz, 2 H), 2.98 (t, J=6.2 Hz, 2 H), 3.03 (t, J=5.1 Hz, 2 H), 4.41 (t, J=5.3 Hz, 2 H), 6.82 (d, J=9.0 Hz, 1 H), 8.11 (dd, J=8.8 and 2.4 Hz, 1 H) MW 343.390 (calc'd); MS (M+H)$^+$344.

Example 5a

The following compounds are prepared essentially according to the procedures set forth above with respect to Examples 1, 2, 3 and 4.
a) 4-Oxo-4,5,6,7,4-tetrahydro-1H-indazole-3-carboxylic acid 3-Fluoro-{4-[2-(propylamino)ethoxy]}phenylamide
b) 4-Oxo-4,5,6,7,4-tetrahydro-1H-indazole-3-carboxylic acid 3-Fluoro-{4-[2-(ethylamino)ethoxy]}phenylamide
c) 4-Oxo-4,5,6,7,4-tetrahydro-1H-indazole-3-carboxylic acid 3-Fluoro-[(6-propylamino)-pyridizin-3-yl]amide
d) 4-Oxo-4,5,6,7,4-tetrahydro-1H-indazole-3-carboxylic acid 3-Fluoro-[(6-butylamino)-pyridizin-3-yl]amide
e) 4-Oxo-4,5,6,7,4-tetrahydro-1H-indazole-3-carboxylic acid 4-[2-(dimethylamino)ethoxy]phenylamide
f) 4-Oxo-4,5,6,7,4-tetrahydro-1H-indazole-3-carboxylic acid [6-(3-(dimethylamino)propoxy)-pyridyl-3-yl]-amide g) 4-Oxo-4,5,6,7,4-tetrahydro-1H-indazole-3-carboxylic acid [6-(3-(diethylamino)propoxy)-pyridyl-3-yl]-amide h) 4-Oxo-6,6-dimethyl-4,5,6,7,4-tetrahydro-1H-indazole-3-carboxylic acid [6-(3-(diethylamino)propoxy)-pyridyl-3-yl]-amide Example 6

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph. In addition, tritium may also be introduced by tritium-halogen exchange with tritium gas, transition metal catalyzed tritium gas reduction of unsaturated bonds, or sodium borotritide reduction of ketones, aldehydes, and imines.

Example 7

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 8

Binding Assay

This assay is a standard assay for $GABA_A$ binding affinity. The high affinity and high selectivity of compounds of this invention for the benzodiazepine site of the $GABA_A$ receptor is confirmed using the binding assay described in Thomas and Tallman (J. Bio. Chem. 1981; 156:9838–9842, and J. Neurosci. 1983; 3:433–440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed and resuspended in 25 volumes of Buffer A (original wt/vol), centrifuged at 20,000×g and the supernatant decanted. This wash step is repeated once. The pellet is finally resuspended in 50 volumes of Buffer A.

Incubations containing 100 µl of tissue homogenate, 100 µl of radioligand, (0.5 nM $^{3}H$-Ro15-1788 [$^{3}H$-Flumazenil], specific activity 80 Ci/mmol), and test compound or control (see below), and are brought to a total volume of 500 µl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 µM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}M$ to $10^{-5}M$ obtained per curve by the method described above for determining percent inhibition. $K_i$ values are calculated according the Cheng-Prussof equation. When tested using this assay, preferred compounds of Formula I exhibit $K_i$ values of less than 1 uM, more preferred compounds of the invention have $K_i$ values of less than 500 nM, and particularly preferred compounds have $K_i$ values of less than 100 nM.

Example 9

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313–1316, 1995) and White, Gurley, Hartnett, Stirling, and Gregory (Receptors and Channels 3: 1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $α_1β_2γ_2$, $α_2β_3γ_2$, $α_3β_3γ_2$, and $α_5β_3γ_2$. Preferably all of the subunit cRNAs in each combination are human clones or all are rat clones. The sequence of each of these cloned subunits is available from GENBANK, e.g., human $α_1$, GENBANK accession no. X14766, human $α_2$, GENBANK accession no. A28100; human $α_3$, GENBANK accession no. A28102; human $α_5$, GENBANK accession no. A28104; human $β_2$, GENBANK accession no. M82919; human $β_3$, GENBANK accession no. Z20136; human $β_2$, GENBANK accession no. X15376; rat $α_1$, GENBANK accession no. L08490, rat $α_2$, GENBANK accession no. L08491; rat $α_3$, GENBANK accession no. L08492; rat $α_5$, GENBANK accession no. L08494; rat $β_2$, GENBANK accession no. X15467; rat $β_3$, GENBANK accession no. X15468; and rat $γ_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evokable GABA current (e.g. 1 µM–9 µM). Each oocyte is exposed to increasing concentrations of compound in order to evaluate a concentration/effect relationship. Compound efficacy is calculated as a percent-change in current amplitude: 100*((Ic/I)−1), where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

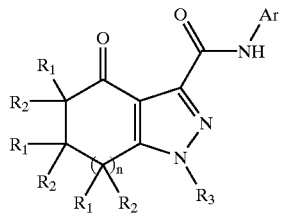

or a pharmaceutically acceptable salt thereof, wherein:

n is 0, 1, or 2;

$R_1$ and $R_2$ are independently selected from hydrogen, halogen, hydroxy, alkyl, alkenyl, alkynyl, alkoxy, haloalkyl, haloalkoxy, nitro, cyano, amino, and mono- or dialkylamino;

$R_3$ is hydrogen or $C_{1-6}$ alkyl;

Ar is pyridyl or pyridizinyl each of which is optionally substituted with 1, 2, 3, or 4 substituents independently selected from the group consisting of halogen, cyano, hydroxy, nitro, azido, alkanoyl, amino, mono or dialkylamino, haloalkoxy, carboxamido, alkyl, alkenyl, alkynyl, alkoxy, cycloalkyl, cycloalkylalkyl, haloalkyl, haloalkenyl, haloalkynyl, aryloxy, alkylthio, alkylsulfinyl, alkylsulfonyl, aminoalkyl, aryl, arylalkyl, arylalkoxy, heteroaryl, and heterocycloalkyl;

when n is 0 or 2, Ar is optionally substituted with G where G represents a group of the formula:

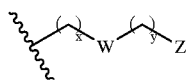

where

W is oxygen, NH, N-alkyl, N-acyl, sulfur, or $CR_5R_6$ where $R_5$ and $R_6$ are the same or different and represent hydrogen, alkyl, or $R_5$ and $R_6$ may be taken together to form a saturated or partially unsaturated carbocyclic ring having 3–7 carbon atoms;

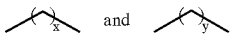

independently represent straight or branched carbon chains which may be substituted with one, two or three substituents independently selected from the group consisting of halogen, hydroxy, cyano, nitro, amino, mono or dialkylamino, alkyl, alkenyl, alkynyl, cycloalkyl, alkoxy, haloalkyl, and haloalkoxy;

x is 0, 1, 2, or 3; and y is 0, 1, 2, or 3; and

Z is hydrogen, hydroxy, alkoxy, cycloalkyl, cycloalkyl (alkoxy), amino, mono or dialkylamino, or —$NR_7COR_8$ where $R^7$ and $R^8$ are the same or different and represent hydrogen or alkyl, or $R_7$ and $R_8$ and the atoms to which they are attached form a heterocycloalkyl ring, or Z is aryl or a saturated, partially unsaturated, or aromatic heterocyclic group of from 1 to 3 rings, 5 to 8 ring members in each ring and, in at least one of said rings, from 1 to about 3 heteroatoms selected from the group consisting of N, O, and S, wherein each aryl or heterocyclic group is optionally substituted on each ring with 1, 2, 3, or 4 substituents independently selected from the group consisting of halogen, cyano, hydroxy, nitro, azido, alkanoyl, carboxamido, alkyl, alkenyl, alkynyl, alkoxy, aryloxy, alkylthio, alkylsulfinyl, alkylsulfonyl, aminoalkyl, aryl, haloalkoxy, amino, mono or dialkylamino, cycloalkyl, cycloalkylalkyl, haloalkyl, haloalkenyl, haloalkynyl, arylalkyl, arylalkoxy, heteroaryl, and heterocycloalkyl; or when n is 1, Ar is substituted with at least one group G where G represents

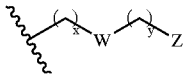

wherein
(i) W is sulfur, and

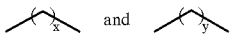

and Z are as defined above;

(ii) W is oxygen, or $NR_{10}$ where $R_{10}$ is hydrogen, alkyl, or acyl, wherein:

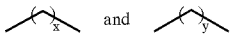

and independently represent straight or branched carbon chains which may be substituted with one, two or three substituents independently selected from the group consisting of halogen, hydroxy, cyano, nitro, amino, mono or dialkylamino, alkyl, alkenyl, alkynyl, cycloalkyl, alkoxy, haloalkyl, and haloalkoxy;

x is 0, 1, 2, or 3; and y is 1, 2, or 3; and

Z is hydroxy, alkoxy, cycloalkyl, cycloalkyl (alkoxy), amino, mono or dialkylamino, or —NR$_7$COR$_8$ where R$_7$ and R$_8$ are the same or different and represent hydrogen or alkyl, or R$_7$ and R$_8$ and the atoms to which they are attached form a heterocycloalkyl ring, or Z is aryl or a saturated, partially unsaturated, or aromatic heterocyclic group of from 1 to 3 rings, 5 to 8 ring members in each ring and, in at least one of said rings, from 1 to about 3 heteroatoms selected from the group consisting of N, O, and S, wherein each aryl or heterocyclic group is optionally substituted on each ring with 1, 2, 3, or 4 substituents independently selected from the group consisting of halogen, cyano, hydroxy, nitro, azido, alkanoyl, carboxamido, alkyl, alkenyl, alkynyl, alkoxy, aryloxy, alkylthio, alkylsulfinyl, alkylsulfonyl, aminoalkyl, aryl, haloalkoxy, amino, mono or dialkylamino, cycloalkyl, cycloalkylalkyl, haloalkyl, haloalkenyl, haloalkynyl, arylalkyl, arylalkoxy, heteroaryl, and heterocycloalkyl;

(iii) W is CR$_5$R$_6$ where R$_5$ and R$_6$ are taken together to form a saturated or partially unsaturated carbocyclic ring, wherein

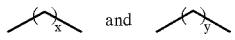 and independently represent straight or branched carbon chains which may be substituted with one, two or three substituents independently selected from the group consisting of halogen, hydroxy, cyano, nitro, amino, mono or dialkylamino, alkyl, alkenyl, alkynyl, cycloalkyl, alkoxy, haloalkyl, and haloalkoxy;

x is 1, 2, or 3; and y is 0, 1, 2, or 3; and

Z is hydrogen, hydroxy, alkoxy, cycloalkyl, cycloalkyl(alkoxy), amino, mono or dialkylamino, or —NR$_7$COR$_8$ where R$_7$ and R$_8$ are the same or different and represent hydrogen or alkyl, or R$_7$ and R$_8$ and the atoms to which they are attached form a heterocycloalkyl ring, or Z is aryl or a saturated, partially unsaturated, or aromatic heterocyclic group of from 1 to 3 rings, 5 to 8 ring members in each ring and, in at least one of said rings, from 1 to about 3 heteroatoms selected from the group consisting of N, O, and S, wherein each aryl or heterocyclic group is optionally substituted on each ring with 1, 2, 3, or 4 substituents independently selected from the group consisting of halogen, cyano, hydroxy, nitro, azido, alkanoyl, carboxamido, alkyl, alkenyl, alkynyl, alkoxy, aryloxy, alkylthio, alkylsulfinyl, alkylsulfonyl, aminoalkyl, aryl, haloalkyl, haloalkoxy, amino, mono or dialkylamino, cycloalkyl, cycloalkylalkyl, haloalkenyl, haloalkynyl, arylalkyl, arylalkoxy, heteroaryl, and heterocycloalkyl.

2. A compound or salt according to claim 1, wherein n is 1;

Ar is pyridyl or pyridizinyl, each of which is substituted with at least one group G and optionally mono-, di-, or trisubstituted with substituents independently chosen from halogen, cyano, nitro, $C_{1-6}$haloalkoxy, hydroxy, amino, $C_{1-6}$ alkyl, $C_{2-6}$ alkenyl, $C_{2-6}$ alkynyl, $C_{3-7}$cycloalkyl, $C_{3-7}$cycloalkyl($C_{1-3}$)alkyl, halo($C_{1-3}$)alkyl, halo($C_{2-3}$)alkenyl, halo($C_{2-3}$)alkynyl, $C_{1-6}$ alkoxy, and mono or di($C_{1-6}$)alkylamino;

wherein G represents

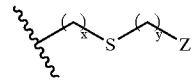

where

Z is hydrogen, hydroxy, alkoxy, cycloalkyl, cycloalkyl (alkoxy), amino, mono or dialkylamino, or —NR$_7$COR$_8$ where R$_7$ and R$_8$ are the same or different and represent hydrogen or alkyl, or Z is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, quinoxalinyl, morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{2-6}$alkenyl, $C_{2-6}$alkynyl, $C_{3-7}$cycloalkyl, $C_{3-7}$cycloalkyl($C_{1-3}$)alkyl, $C_{1-3}$haloalkoxy, halo($C_{1-3}$)alkyl, halo($C_{2-3}$)alkenyl, halo($C_3$)alkynyl, $C_{1-6}$alkoxy, and mono or di($C_{1-6}$)alkylamino; and

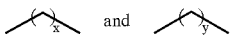 and independently represent straight or branched carbon chains which may be substituted with one, two or three substituents independently selected from the group consisting of hydroxy, halogen, cyano, nitro, amino, mono or di($C_{1-6}$)alkylamino, $C_{1-6}$alkyl, $C_{2-6}$alkenyl, $C_{2-6}$alkynyl, $C_{3-7}$cycloalkyl, $C_{1-6}$alkoxy, $C_{1-6}$haloalkyl, and $C_{1-6}$haloalkoxy;

x is 0, 1, 2, or 3; and y is 0, 1, 2, or 3.

3. A compound or salt according to claim 2, wherein

Ar is pyridyl or pyridizinyl, each of which is substituted with at least one group G and optionally mono-, di-, or trisubstituted with substituents independently chosen from halogen, cyano, nitro, hydroxy, amino, $C_{1-6}$alkyl, $C_{2-6}$alkenyl, $C_{2-6}$ alkynyl, $C_{3-7}$cycloalkyl, $C_{3-7}$cycloalkyl($C_{1-3}$)alkyl, halo($C_{1-3}$)alkyl, halo($C_{1-3}$)alkoxy, halo($C_{2-3}$)alkenyl, halo($C_{2-3}$)alkynyl, $C_{1-6}$ alkoxy, and mono or di($C_{1-6}$)alkylamino;

Z is hydrogen, hydroxy, $C_{1-6}$alkoxy, $C_{3-7}$cycloalkyl, $C_{3-7}$cycloalkyl($C_{1-3}$alkoxy), amino, mono or di($C_{1-6}$)alkylamino, or —NR$_7$COR$_8$ where R$_7$ and R$_8$ are the same or different and represent hydrogen or $C_{1-6}$alkyl, or

37

Z is morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{3-7}$ cycloalkyl, $C_{3-7}$ cycloalkyl($C_{1-3}$)alkyl, halo($C_{1-3}$)alkyl, halo($C_{1-3}$)alkoxy, $C_{1-6}$ alkoxy, or mono and di($C_{1-6}$)alkylamino; and

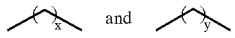

independently represent methylene groups;
where
x is 0, 1, 2, or 3; and
y is 0, 1, 2, or 3.

4. A compound or salt according to claim 3, wherein x is 0.

5. A compound or salt according to claim 4, wherein
Z is hydrogen, hydroxy, $C_{1-6}$ alkoxy, $C_{3-7}$cycloalkyl ($C_{1-3}$ alkoxy), amino, or mono or di($C_{1-6}$)alkylamino, or
Z is morpholinyl, pyrrolidnyl, piperidinyl, or piperazinyl, each of which is optionally mono-, di-, or trisubstituted independently with substituents independently chosen from halogen, amino, cyano, nitro, $C_{1-6}$haloalkyoxy, hydroxy, $C_{1-6}$alkyl, $C_{3-7}$cycloalkyl, $C_{3-7}$cycloalkyl ($C_{1-3}$)alkyl, halo($C_{1-3}$)alkyl, halo($C_{1-3}$)alkoxy, $C_{1-6}$ alkoxy, and mono or di($C_{1-6}$) alkylamino.

6. A compound or salt according to claim 4, wherein
Z is amino, mono or di($C_{1-6}$)alkylamino, or
Z is morpholinyl, pyrrolidinyl, piperidinyl, or piperazinyl, each of which is optionally mono- or disubstituted with substituents independently chosen from halogen, amino, cyano, nitro, $C_{1-2}$haloalkyl, $C_{1-2}$haloalkoxy, hydroxy, $C_{1-6}$ alkyl, $C_{1-6}$ alkoxy, and mono or di($C_{1-6}$) alkylamino.

7. A compound or salt according to claim 1, wherein
n is 1;
Ar is pyridyl or pyridizinyl, each of which is substituted with at least one group G and optionally mono-, di-, or trisubstituted with halogen, cyano, nitro, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkyl, halo($C_{1-3}$)alkoxy, halo($C_{2-3}$)alkenyl, halo($C_{2-3}$) alkynyl, $C_{1-6}$ alkoxy, or mono or di($C_{1-6}$) alkylamino;
wherein G represents

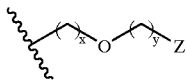

where

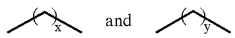

independently represent straight or branched carbon chains which may be substituted with one, two or three substituents independently selected from the group consisting of hydroxy, halogen, cyano, nitro, amino, mono or di($C_{1-6}$)alkylamino, $C_{1-6}$alkyl $C_{2-6}$alkenyl, $C_{3-7}$cycloalkyl, $C_{1-6}$alkoxy, $C_{1-6}$haloalkyl, and $C_{1-6}$haloalkoxy;
x is 0, 1, or 2;
y is 1, 2, or 3; and
Z is hydroxy, $C_{1-6}$alkyl, $C_{3-7}$cycloalkyl ($C_{1-3}$alkoxy), amino, mono or di($C_{1-6}$)alkylamino, or —NR$_7$COR$_8$ where

38

R$_7$ and R$_8$ are the same or different and represent hydrogen or $C_{1-6}$alkyl, or
Z is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, quinoxalinyl, morpholinyl, pyrrolidinyl, piperidinyl, pyridizinyl, or piperazinyl, each of which is optionally mono-, di-, or trisubstituted with substituents independently chosen from halogen, amino, cyano, nitro, hydroxy, $C_{1-6}$ alkyl, $C_{2-6}$ alkenyl, $C_{2-6}$ alkynyl, $C_{3-7}$ cycloalkyl, $C_{3-7}$ cycloalkyl ($C_{1-3}$)alkyl, halo($C_{1-3}$) alkyl, halo($C_{1-3}$)alkoxy, halo($C_{2-3}$)alkenyl, halo($C_{2-3}$) alkynyl, $C_{1-6}$ alkoxy, and mono or di($C_{1-6}$)alkylamino.

8. A compound or salt according to claim 7, wherein
Ar is pyridyl or pyridizinyl, each of which is substituted with at least one group G and optionally mono-, di-, or trisubstituted with substituents independently chosen from halogen, cyano, nitro, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkoxy, halo($C_{1-3}$) alkyl, halo($C_{2-3}$)alkenyl, halo($C_{2-3}$)alkynyl, $C_{1-6}$ alkoxy, and mono or di($C_{1-6}$)alkylamino;
Z is hydroxy, alkoxy, cycloalkyl(alkoxy), amino, mono- or di($C_1$–$C_6$)alkylamino, or —NR$_7$COR$_8$ where R$_7$ and R$_8$ are the same or different and represent hydrogen or $C_1$–$C_6$ alkyl, or
Z is morpholinyl, pyrrolidinyl, piperidinyl, or piperazinyl, each of which is optionally mono-, di-, or trisubstituted with substituents independently chosen from halogen, amino, cyano, nitro, trifluoromethyl, trifluoromethoxy, hydroxy, $C_{1-6}$ alkyl, $C_{3-7}$ cycloalkyl, $C_{3-7}$ cycloalkyl ($C_{1-3}$)alkyl, halo($C_{1-3}$)alkyl, $C_{1-6}$ alkoxy, and mono or di($C_{1-6}$)alkylamino; and

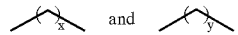

independently represent methylene groups;
where
x is 0, 1, 2, or 3; and
y is 1, 2, or 3.

9. A compound or salt according to claim 8, wherein x is 0.

10. A compound or salt according to claim 9, wherein
Z is hydroxy, $C_1$–$C_6$ alkoxy, $C_3$–$C_7$ cycloalkyl($C_1$–$C_6$) alkoxy, amino, or mono- or di($C_1$–$C_6$)alkylamino, or
Z is morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{3-7}$ cycloalkyl, $C_{3-7}$ cycloalkyl($C_{1-3}$)alkyl, halo($C_{1-3}$)alkyl, halo ($C_{1-3}$)alkoxy, $C_{1-6}$ alkoxy, and mono or di($C_{1-6}$) alkylamino.

11. A compound or salt according to claim 9, wherein
y is 1, 2, or 3;
Z is amino, or mono- or di($C_1$–$C_4$)alkylamino, or
Z is morpholinyl, pyrrolidinyl, piperidinyl, or piperazinyl, each of which is optionally mono- or disubstituted independently with $C_{1-6}$ alkyl, or mono or di($C_{1-6}$) alkylamino.

12. A compound or salt according to claim 9, wherein

Z is amino, mono or di($C_1$–$C_6$)alkylamino, or

Z is morpholinyl, pyrrolidinyl, piperidinyl, or piperazinyl, each of which is optionally mono- or disubstituted independently with $C_{3-7}$ cycloalkyl, $C_{3-7}$ cycloalkyl($C_{1-3}$)alkyl, or $C_{1-6}$ alkyl.

13. A compound or salt according to claim 9, wherein Z is mono or di($C_1$–$C_3$)alkylamino.

14. A compound or salt according to claim 9, wherein y is 1, 2, or 3 and Z is $C_1$–$C_3$ alkylamino.

15. A compound or salt according to claim 13, wherein $R_1$ and $R_2$ are independently selected from hydrogen, halogen, hydroxy, $C_{1-6}$ alkyl, $C_{2-6}$ alkenyl, $C_{2-6}$ alkynyl, $C_{1-6}$ alkoxy, $C_{1-2}$haloalkyl, $C_{1-2}$haloalkoxy, nitro, cyano, amino, and mono- and di($C_{1-6}$)alkylamino.

16. A compound or salt according to claim 14, wherein $R_1$ and $R_2$ are independently selected from the group consisting of hydrogen, halogen, hydroxy, $C_{1-2}$ alkyl, $C_{1-2}$ alkoxy, $C_{1-2}$ haloalkyl, and $C_{1-2}$haloalkoxy.

17. A compound or salt according to claim 1, wherein n is 1;

Ar is pyridyl or pyridizinyl, each of which is substituted with at least one group G and optionally mono-, di-, or trisubstituted with substituents independently chosen from halogen, cyano, nitro,hydroxy, amino, $C_{1-6}$alkyl, $C_{2-6}$ alkenyl, $C_{2-6}$ alkynyl, $C_{3-7}$ cycloalkyl, $C_{3-7}$cycloalkyl($C_{1-3}$)alkyl, halo($C_{1-3}$)alkyl, halo($C_{1-3}$)alkoxy, halo($C_{2-3}$)alkenyl, halo($C_{2-3}$)alkynyl, $C_{1-6}$ alkoxy, and mono or di($C_{1-6}$)alkylamino;

wherein G represents

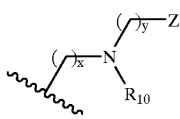

where $R_{10}$ is hydrogen, $C_{1-6}$ alkyl, or $C_{2-6}$ acyl;

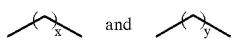

independently represent straight or branched carbon chains which may be substituted with one, two or three substituents independently selected from the group consisting of hydroxy, halogen, cyano, nitro, amino, mono or di($C_{1-6}$)alkylamino, $C_{1-6}$alkyl, $C_{2-6}$alkenyl, $C_{3-7}$cycloalkyl, $C_{1-6}$alkoxy, $C_{1-6}$haloalkyl, and $C_{1-6}$haloalkoxy;

x is 0, 1, or 2;

y is 1, 2, or 3; and

Z is hydroxy, alkoxy, $C_{3-7}$cycloalkyl ($C_{1-3}$alkoxy), amino, mono or di($C_{1-6}$)alkylamino, or —$NR_7COR_8$ where $R_7$ and $R_8$ are the same or different and represent hydrogen or $C_{1-6}$alkyl, or Z is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, quinoxalinyl, morpholinyl, pyrrolidinyl, piperidinyl, pyridizinyl, or piperazinyl, each of which is optionally mono-, di-, or trisubstituted with substituents independently chosen from halogen, amino, cyano, nitro, hydroxy, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$) alkyl, halo($C_{1-3}$)alkoxy, halo($C_{2-3}$)alkenyl, halo($C_{2-3}$)alkynyl, $C_{1-6}$ alkoxy, and mono or di($C_{1-6}$) alkylamino.

18. A compound or salt according to claim 17, wherein $R_{10}$ is hydrogen or $C_1$–$C_6$ alkyl;

Ar is pyridyl or pyridizinyl, each of which is substituted with at least one group G and optionally mono-, di-, or trisubstituted with substituents independently chosen from halogen, cyano, nitro, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkoxy, halo($C_{1-3}$) alkyl, halo($C_{2-3}$)alkenyl, halo($C_{2-3}$)alkynyl, $C_{1-6}$ alkoxy, and mono or di($C_{1-6}$)alkylamino;

Z is hydroxy, alkoxy, cycloalkyl(alkoxy), amino, mono- or di($C_1$–$C_6$)alkylamino, or —$NR_7COR_8$ where $R_7$ and $R_8$ are the same or different and represent hydrogen or $C_1$–$C_6$ alkyl, or Z is morpholinyl, pyrrolidinyl, piperidinyl, or piperazinyl, each of which is optionally mono-, di-, or trisubstituted with substituents independently chosen from halogen, amino, cyano, nitro, trifluoromethyl, trifluoromethoxy, hydroxy, $C_{1-6}$ alkyl, $C_{3-7}$ cycloalkyl, $C_{3-7}$ cycloalkyl ($C_{1-3}$)alkyl, halo($C_{1-3}$) alkyl, $C_{1-6}$ alkoxy, and mono or di($C_{1-6}$)alkylamino; and

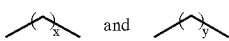

independently represent methylene groups;

where x is 0, 1, 2, or 3; and y is 1, 2, or 3.

19. A compound or salt according to claim 18, wherein x is 0 and $R_{10}$ is hydrogen or methyl.

20. A compound or salt according to claim 19, wherein

Z is hydroxy, $C_1$–$C_6$ alkoxy, $C_3$–$C_7$ cycloalkyl($C_1$–$C_6$) alkoxy, amino, or mono- or di($C_1$–$C_6$)alkylamino, or Z is morpholinyl, pyrrolidinyl, piperidinyl, or piperazinyl, each of which is optionally mono-, di-, or trisubstituted with substituents independently chosen from halogen, amino, cyano, nitro, hydroxy, $C_{1-6}$ alkyl, $C_{3-7}$ cycloalkyl, $C_{3-7}$ cycloalkyl ($C_{1-3}$)alkyl, halo($C_{1-3}$) alkyl, halo ($C_{1-3}$)alkoxy, $C_{1-6}$ alkoxy, and mono or di($C_{1-6}$)alkylamino.

21. A compound or salt according to claim 19, wherein y is 1, 2, or 3;

Z is amino, or mono- or di($C_1$–$C_4$)alkylamino, or

Z is morpholinyl, pyrrolidinyl, piperidinyl, or piperazinyl, each of which is optionally mono- or disubstituted independently with $C_{1-6}$ alkyl, or mono or di($C_{1-6}$) alkylamino.

22. A compound or salt according to claim 19, wherein

Z is amino, mono or di($C_1$–$C_6$)alkylamino, or

Z is morpholinyl, pyrrolidinyl, piperidinyl, or piperazinyl, each of which is optionally mono- or disubstituted independently with $C_{3-7}$ cycloalkyl, $C_{3-7}$ cycloalkyl ($C_{1-3}$)alkyl, or $C_{1-6}$ alkyl.

23. A compound or salt according to claim 19, wherein Z is mono or di($C_1$–$C_3$)alkylamino.

24. A compound or salt according to claim 19, wherein y is 1, 2, or 3 and Z is $C_1$–$C_2$ alkylamino.

25. A compound or salt according to claim 23, wherein $R_1$ and $R_2$ are independently selected from hydrogen, halogen, hydroxy, $C_{1-6}$ alkyl, $C_{2-6}$ alkenyl, $C_{2-6}$ alkynyl, $C_{1-6}$ alkoxy, $C_{1-2}$haloalkyl, $C_{1-2}$haloalkoxy, nitro, cyano, amino, and mono- and di($C_{1-6}$)alkylamino.

26. A compound or salt according to claim 24, wherein $R_1$ and $R_2$ are independently selected from the group consisting of hydrogen, halogen, hydroxy, $C_{1-2}$ alkyl, $C_{1-2}$ alkoxy, $C_{1-2}$haloalkyl, and $C_{1-2}$haloalkoxy.

27. A compound or salt according to claim 5, wherein $R_3$ is hydrogen.

28. A compound or salt according to claim 9, wherein $R_3$ is hydrogen.

29. A compound or salt according to claim 14, wherein $R_3$ is hydrogen.

30. A compound or salt according to claim 26, wherein $R_3$ is hydrogen.

31. A compound or salt according to claim 1, wherein
n is 0 or 2;
$R_1$ and $R_2$ are independently selected from the group consisting of hydrogen, halogen, hydroxy, $C_{1-2}$ alkyl, $C_{1-2}$ alkoxy, $C_{1-2}$haloalkyl, and $C_{1-2}$haloalkoxy;
Ar is pyridyl or pyridizinyl, each of which is optionally mono-, di-, or trisubstituted with substituents independently chosen from halogen, cyano, nitro, $C_{1-6}$haloalkoxy, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkyl, halo($C_{2-3}$)alkenyl, halo($C_{2-3}$)alkynyl, $C_{1-6}$ alkoxy, mono or di($C_{1-6}$)alkylamino and G; wherein G represents

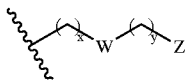

where
W is nitrogen, oxygen, or $CR_5R_6$ where $R_5$ and $R_6$ are the same or different and represent hydrogen or straight or branched chain $C_{1-6}$ alkyl;
Z is selected from the group consisting of hydrogen, hydroxy, $C_{2-6}$alkoxy, $C_{3-7}$cycloalkyl, $C_{3-7}$cycloalkyl($C_{1-3}$alkoxy), amino, and mono or di($C_{1-6}$)alkylamino; or
Z is piperidinyl, piperazinyl, pyrrolidinyl, morpholinyl, phenyl, pyridyl, pyrazolyl, pyrimidinyl, or pyridizinyl, each of which is optionally substituted with one, two, or three groups independently selected from the group consisting of halo($C_1-C_6$)alkyl, halo($C_1-C_6$)alkoxy, halogen, $C_{1-6}$ alkyl, hydroxy, and $C_{1-6}$ alkoxy;

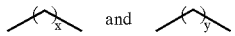

represent straight or branched carbon chains which may be substituted with one, two or three substituents independently selected from the group consisting of hydroxy, halogen, amino, mono or di($C_{1-6}$)alkylamino, $C_{1-6}$ alkoxy, $C_{2-6}$alkenyl, $C_{2-6}$ alkynyl, $C_{3-7}$cycloalkyl, $C_{1-6}$alkoxy, $C_{1-6}$haloalkyl, and $C_{1-6}$haloalkoxy;
x is 0, 1, 2, or 3; and
y is 0, 1, 2, or 3.

32. A compound according to claim 31, wherein
Ar is pyridyl or pyridizinyl, each of which is optionally mono-, di-, or trisubstituted with substituents independently chosen from halogen, cyano, nitro, $C_{1-6}$haloalkoxy, hydroxy, amino, $C_{1-6}$ alkyl, $C_{2-6}$ alkenyl, $C_{2-6}$ alkynyl, $C_{3-7}$ cycloalkyl, $C_{3-7}$ cycloalkyl($C_{1-3}$)alkyl, halo($C_{1-3}$)alkyl, halo($C_{2-3}$)alkenyl, halo($C_{2-3}$)alkynyl, $C_{1-6}$ alkoxy, mono or di($C_{1-6}$)alkylamino and G.

33. A compound or salt according to claim 31, wherein
Ar is pyridyl or pyridizinyl, each of which is substituted with at least one G and optionally substituted with one or two groups independently selected from halogen, $C_1-C_6$ alkyl, $C_1l-C_6$ alkoxy, trifluoromethyl, amino, and mono- and di($C_1-C_6$)alkylamino.

34. A compound according to claim 14, wherein $R_1$ and $R_2$ are independently selected at each occurrence from hydrogen, methyl and ethyl.

35. A compound or salt according to claim 34, wherein no more than three of $R_1$ and $R_2$ are other than hydrogen.

36. A compound or salt according to claim 14, wherein one, two, or three of $R_1$ and $R_2$ is methyl or ethyl, and the remaining $R_1$ and $R_2$ substituents are hydrogen.

37. A compound or salt according to claim 6, wherein one, two, or three of $R_1$ and $R_2$ is methyl or ethyl, and the remaining $R_1$ and $R_2$ substituents are hydrogen.

38. A compound or salt according to claim 26, wherein one, two, or three of $R_1$ and $R_2$ is methyl or ethyl, and the remaining $R_1$ and $R_2$ substituents are hydrogen.

39. A compound or salt according to claim 5, wherein Ar is pyridyl or pyridizinyl, each of which is
substituted with one group selected from halogen, $C_1-C_3$ alkyl, $C_1-C_3$ alkoxy, nitro, amino, and mono- and di($C_1-C_2$)alkylamino; and
substituted with $C_1-C_3$ alkoxy substituted with: $C_1-C_3$ alkylamino, di($C_1-C_3$) alkylamino, amino, morpholino, piperazinyl, 4-($C_{1-4}$) alkylpiperazinyl, piperidinyl or piperidinyl optionally substituted with $C_1-C_4$ alkyl.

40. A compound or salt according to claim 9, wherein Ar is pyridyl or pyridizinyl, each of which is
substituted with one group selected from halogen, $C_1-C_3$ alkyl, $C_1-C_3$ alkoxy, nitro, amino, and mono- and di($C_1-C_2$)alkylamino; and
substituted with $C_1-C_3$ alkoxy substituted with: $C_1-C_3$ alkylamino, di($C_1-C_3$)alkylamino, amino, morpholino, piperazinyl, 4-($C_{1-4}$) alkylpiperazinyl, piperidinyl or piperidinyl optionally substituted with $C_1-C_4$ alkyl.

41. A compound or salt according to claim 19, wherein Ar is pyridyl pyridizinyl, each of which is
substituted with one group selected from halogen, $C_1-C_3$ alkyl, $C_1-C_3$ alkoxy, nitro, amino, and mono- and di($C_1-C_2$)alkylamino; and
substituted with $C_1-C_3$ alkoxy substituted with: $C_1-C_3$ alkylamino, di($C_1-C_3$)alkylamino, amino, morpholino, piperazinyl, 4-($C_{1-4}$) alkylpiperazinyl, piperidinyl or piperidinyl optionally substituted with $C_1-C_4$ alkyl.

42. A compound or salt according to claim 1, which is
4-Oxo-4,5,6,7-tetrahydro-1H-indazole-3-carboxylic acid [6-(2-propylamino-ethoxy)-pyridin-3-yl]-amide or a pharmaceutically acceptable salt thereof;
4-Oxo-4,5,6,7-tetrahydro-1H-indazole-3-carboxylic acid [6-(2-ethylamino-ethoxy)-pyridin-3-yl]-amide or a pharmaceutically acceptable salt thereof;
4-Oxo-4,5,6,7,4-tetrahydro-1H-indazole-3-carboxylic acid [6-(3-(dimethylamino)propoxy)-pyridyl-3-yl]-amide or a pharmaceutically acceptable salt thereof;

4-Oxo-4,5,6,7,4-tetrahydro-1H-indazole-3-carboxylic acid [6-(3-(diethylamino)propoxy)-pyridyl-3-yl]-amide or a pharmaceutically acceptable salt thereof; or 4-Oxo-6,6-dimethyl-4,5,6,7,4-tetrahydro-1H-indazole-3-carboxylic acid [6-(3-(diethylamino)propoxy)-pyridyl-3-yl]-amide;

or a pharmaceutically acceptable salt thereof.

43. A compound which is

4-Oxo-4,5,6,7,4-tetrahydro-1H-indazole3carboxylic acid 3-Fluoro-[(6-propylamino)-pyridizin-3-yl]amide or a pharmaceutically acceptable salt thereof; or 4-Oxo-4,5,6,7,4-tetrahydro-1H-indazole3carboxylic acid 3-Fluoro-[(6-butylamino)-pyridizin-3-yl]amide or a pharmaceutically acceptable salt thereof.

44. A pharmaceutical composition comprising a compound or salt according to claim 1 combined with at least one pharmaceutically acceptable carrier or excipient.

45. A pharmaceutical composition comprising a compound or salt according to claim 1 combined with at least one pharmaceutically acceptable carrier or excipient.

* * * * *